(12) United States Patent
Chiu et al.

(10) Patent No.: US 7,912,531 B1
(45) Date of Patent: Mar. 22, 2011

(54) MAGNETIC RESONANCE IMAGING COILS

(75) Inventors: Jessica G Chiu, Belmont, CA (US); Barabara E. Stamberg, San Jose, CA (US); Dagmar Bettina Beyerlein, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2041 days.

(21) Appl. No.: 10/740,311

(22) Filed: Dec. 17, 2003

(51) Int. Cl.
*A61B 5/05* (2006.01)
*G01V 3/00* (2006.01)

(52) U.S. Cl. ......... 600/423; 600/422; 324/309; 324/318

(58) Field of Classification Search ............... 600/437, 600/462–467; 623/1.11, 1.12, 1.2
See application file for complete search history.

(56) References Cited

U.S. PATENT DOCUMENTS

| | | | |
|---|---|---|---|
| 4,857,846 A | 8/1989 | Carlson | |
| 5,263,963 A | 11/1993 | Garrison et al. | |
| 5,413,104 A * | 5/1995 | Buijs et al. | 600/423 |
| 5,451,232 A * | 9/1995 | Rhinehart et al. | 606/192 |
| 5,476,095 A * | 12/1995 | Schnall et al. | 600/423 |
| 5,558,643 A | 9/1996 | Samson et al. | |
| 5,699,801 A * | 12/1997 | Atalar et al. | 600/410 |
| 5,797,878 A | 8/1998 | Bleam | |
| 5,964,705 A | 10/1999 | Truwit et al. | |
| 5,976,106 A | 11/1999 | Verin et al. | |
| 6,011,995 A * | 1/2000 | Guglielmi et al. | 607/99 |
| 6,068,611 A | 5/2000 | Loffler et al. | |
| 6,074,339 A | 6/2000 | Gambale et al. | |
| 6,099,454 A | 8/2000 | Hastings et al. | |
| 6,117,065 A | 9/2000 | Hastings et al. | |
| 6,159,139 A | 12/2000 | Chiu | |
| 6,190,356 B1 | 2/2001 | Bersin | |
| 6,210,312 B1 | 4/2001 | Nagy | |
| 6,216,044 B1 * | 4/2001 | Kordis | 607/122 |
| 6,224,535 B1 | 5/2001 | Chiu et al. | |
| 6,234,952 B1 | 5/2001 | Liprie | |
| 6,234,971 B1 * | 5/2001 | Jang | 600/462 |
| 6,261,246 B1 * | 7/2001 | Pantages et al. | 600/585 |
| 6,364,841 B1 * | 4/2002 | White et al. | 600/466 |
| 6,394,978 B1 * | 5/2002 | Boyle et al. | 604/103.06 |
| 6,437,569 B1 * | 8/2002 | Minkoff et al. | 324/318 |
| 6,516,213 B1 * | 2/2003 | Nevo | 600/424 |
| 6,579,311 B1 * | 6/2003 | Makower | 623/1.23 |
| 6,593,884 B1 * | 7/2003 | Gilboa et al. | 342/448 |

(Continued)

OTHER PUBLICATIONS

Pathway MRI, "1.5 T High Resolution Head Coil—General Information", http://www.pathwaymri.com/products/15T-head/15head.htm, (Jan. 25, 2001), 1 page.

*Primary Examiner* — Long V Le
*Assistant Examiner* — Angela M Hoffa
(74) *Attorney, Agent, or Firm* — Blakely Sokoloff Taylor & Zafman LLP

(57) ABSTRACT

An apparatus including a device such as a catheter or guidewire having dimensions suitable for percutaneous delivery to a patient; and a magnetic resonance (MR) compatible antenna associated with the device in a manner that provides a prescribed radial and/or longitudinal orientation of the antenna at a point of interest within a blood vessel of a patient. An antenna suitable for radial and/or longitudinal orientation. A method including inserting a medical device having an antenna capable of transmitting radio frequency signals in a blood vessel of a patient and radially and/or longitudinally orienting the antenna at a point of interest within a blood vessel of a patient.

37 Claims, 21 Drawing Sheets

U.S. PATENT DOCUMENTS

| | | | |
|---|---|---|---|
| 6,600,319 B2* | 7/2003 | Golan | 324/318 |
| 6,628,980 B2* | 9/2003 | Atalar et al. | 600/423 |
| 6,672,312 B2* | 1/2004 | Acker | 128/898 |
| 6,711,436 B1* | 3/2004 | Duhaylongsod | 607/9 |
| 6,765,144 B1* | 7/2004 | Wang et al. | 174/36 |
| 7,044,964 B2* | 5/2006 | Jang et al. | 623/1.2 |
| 7,291,146 B2* | 11/2007 | Steinke et al. | 606/41 |
| 2002/0156515 A1* | 10/2002 | Jang et al. | 623/1.11 |
| 2003/0028095 A1* | 2/2003 | Tulley et al. | 600/422 |
| 2003/0050557 A1* | 3/2003 | Susil et al. | 600/424 |
| 2003/0105509 A1* | 6/2003 | Jang et al. | 623/1.11 |
| 2003/0160721 A1* | 8/2003 | Gilboa et al. | 342/450 |
| 2003/0187347 A1* | 10/2003 | Nevo et al. | 600/424 |
| 2003/0195412 A1* | 10/2003 | Gillies et al. | 600/411 |
| 2004/0002650 A1 | 1/2004 | Mandrusov et al. | |
| 2004/0153135 A1* | 8/2004 | Haase et al. | 623/1.11 |
| 2004/0162516 A1 | 8/2004 | Mandrusov et al. | |
| 2005/0054914 A1* | 3/2005 | Duerk et al. | 600/423 |
| 2005/0070844 A1 | 3/2005 | Chow et al. | |
| 2005/0096647 A1* | 5/2005 | Steinke et al. | 606/41 |
| 2006/0064009 A1 | 3/2006 | Webler et al. | |
| 2006/0224179 A1* | 10/2006 | Kucharczyk et al. | 606/200 |
| 2006/0265043 A1 | 11/2006 | Mandrusov et al. | |
| 2008/0091223 A1* | 4/2008 | Pokorney et al. | 606/159 |

* cited by examiner

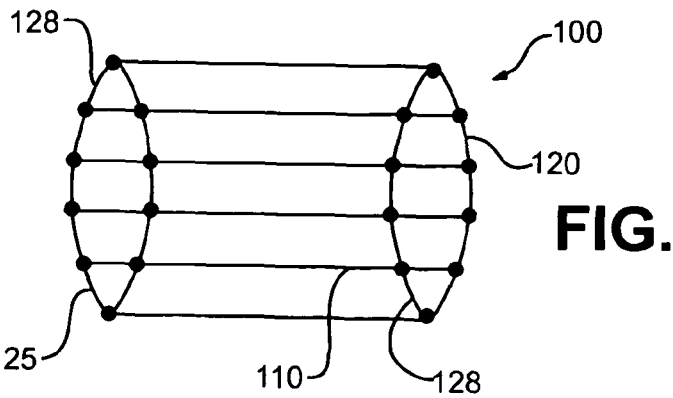
FIG. 1
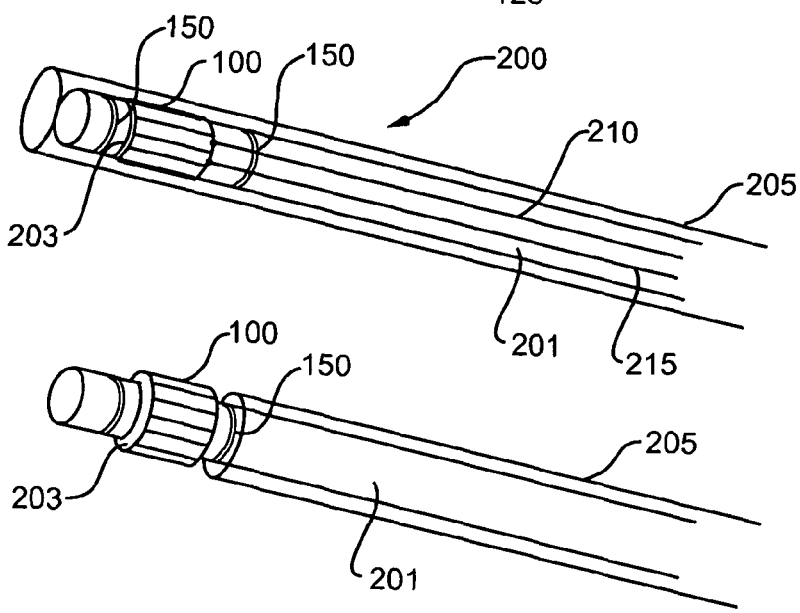
FIG. 1A
FIG. 1B
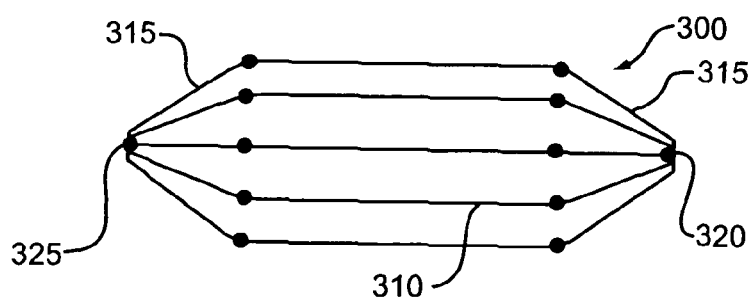
FIG. 2A

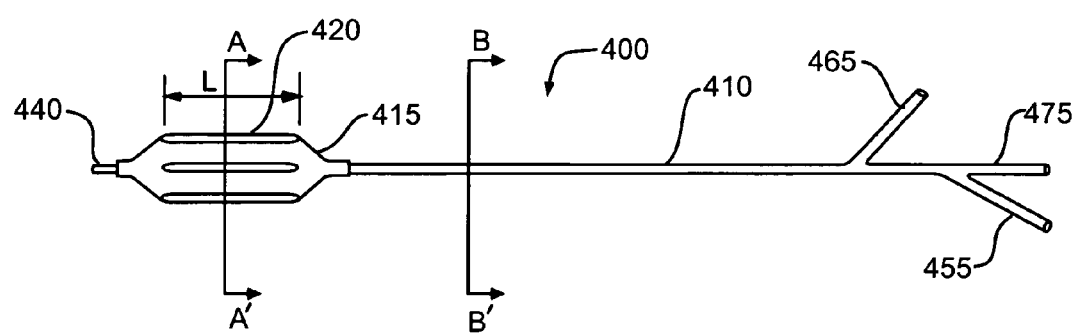
FIG. 3A
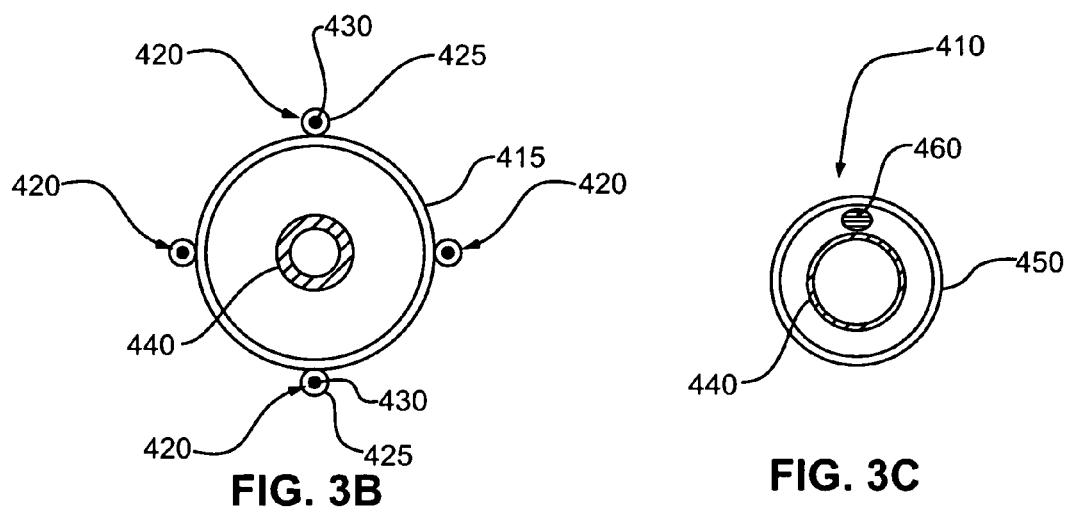
FIG. 3B
FIG. 3C

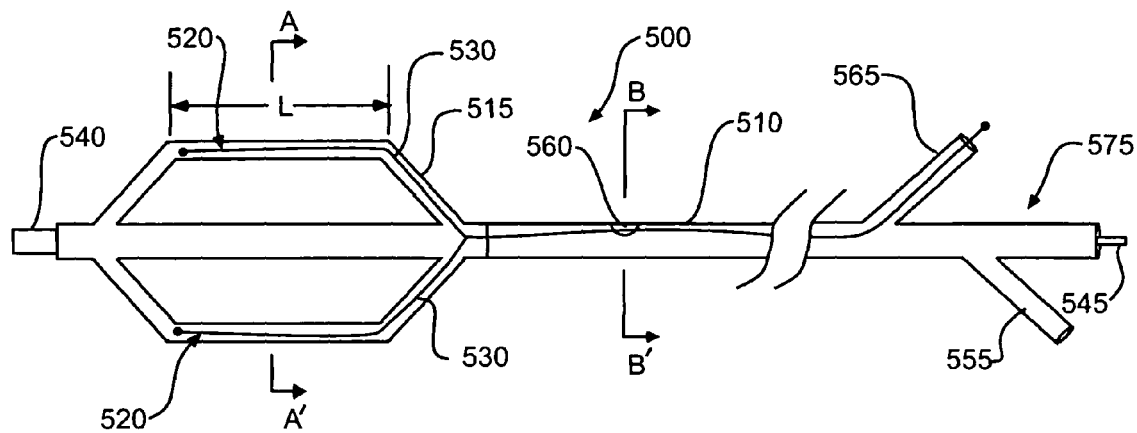
FIG. 4A
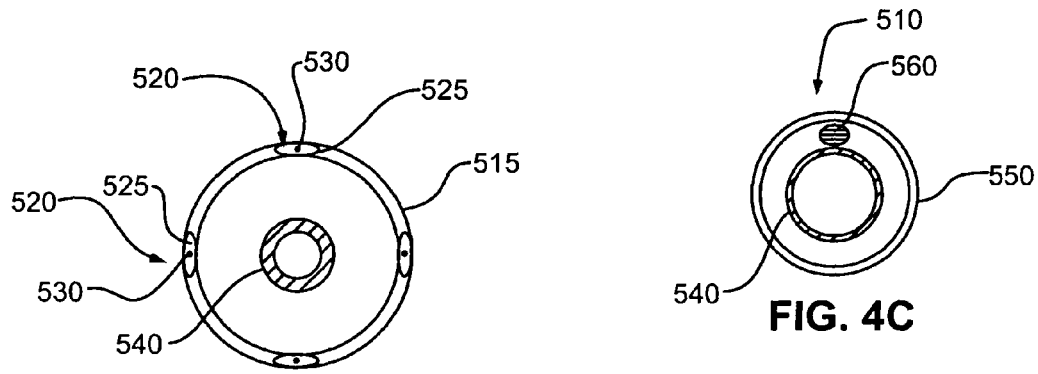
FIG. 4B
FIG. 4C
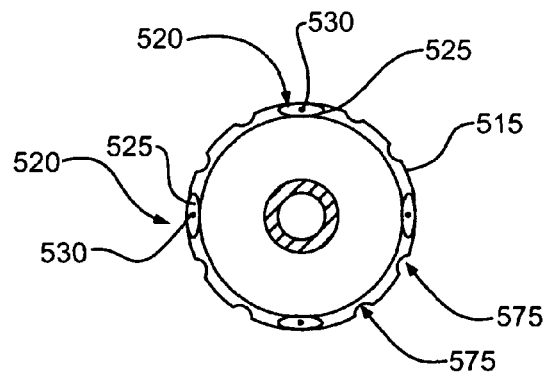
FIG. 4D

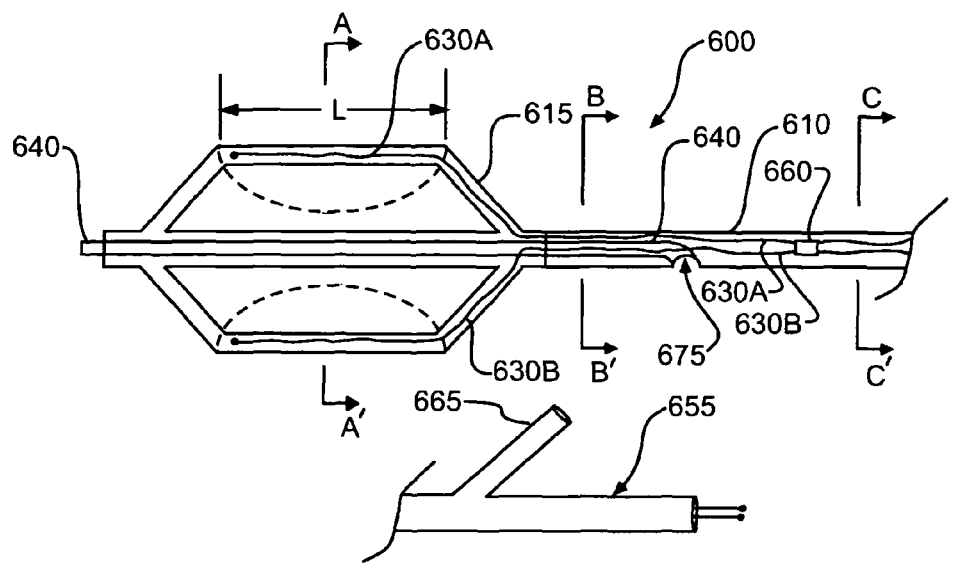
FIG. 5A
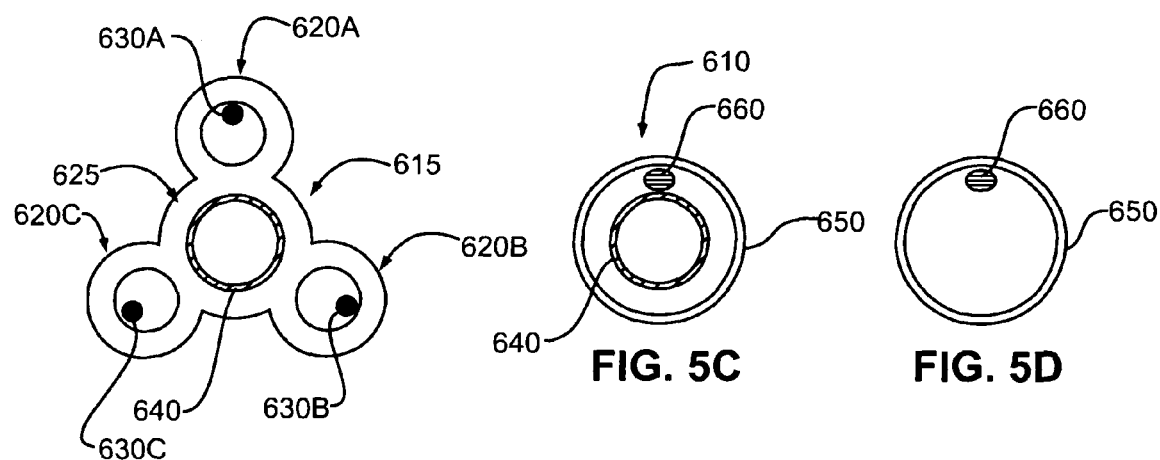
FIG. 5B  FIG. 5C  FIG. 5D

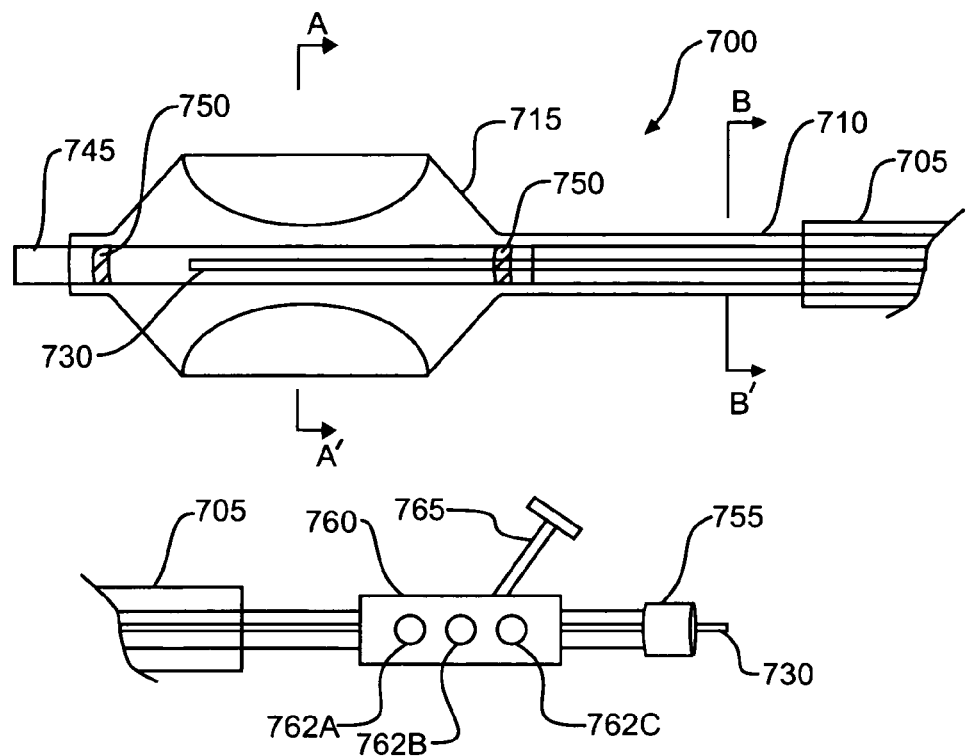
FIG. 6A
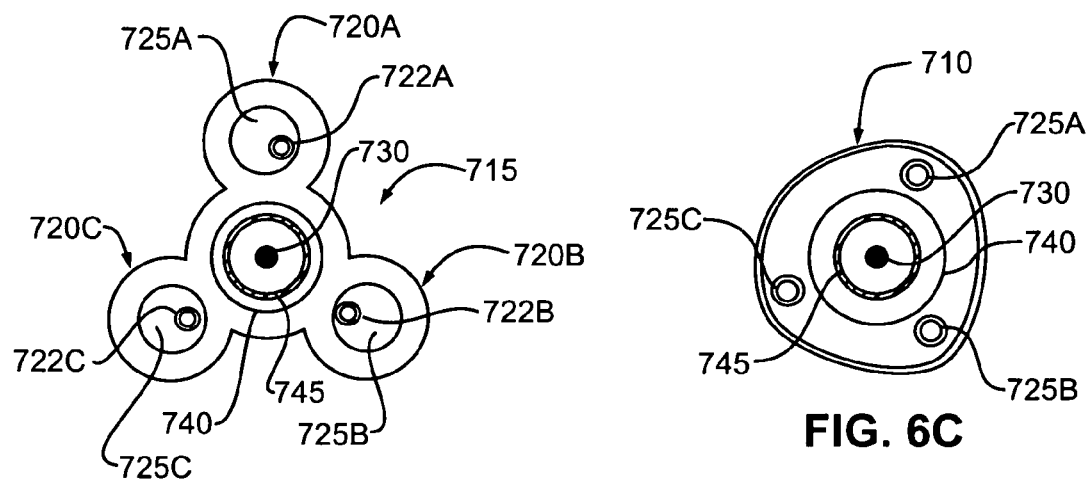
FIG. 6B
FIG. 6C

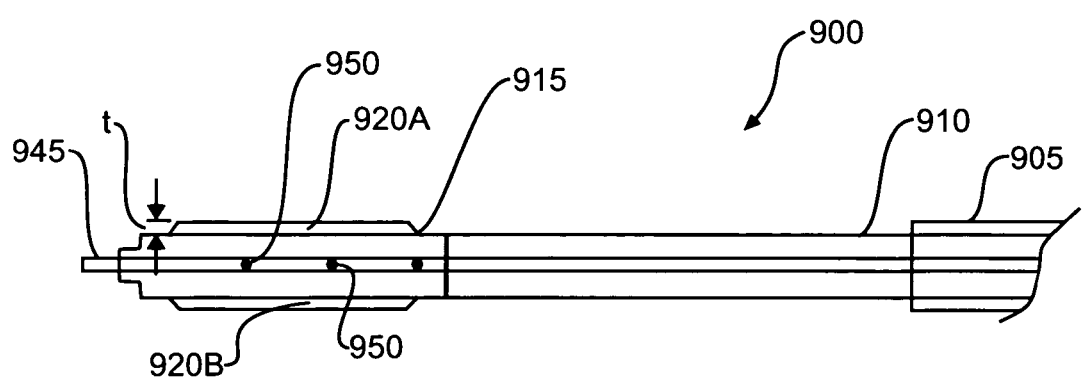
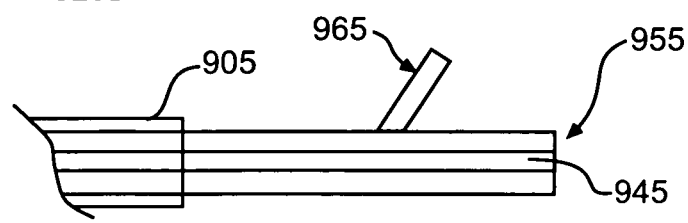
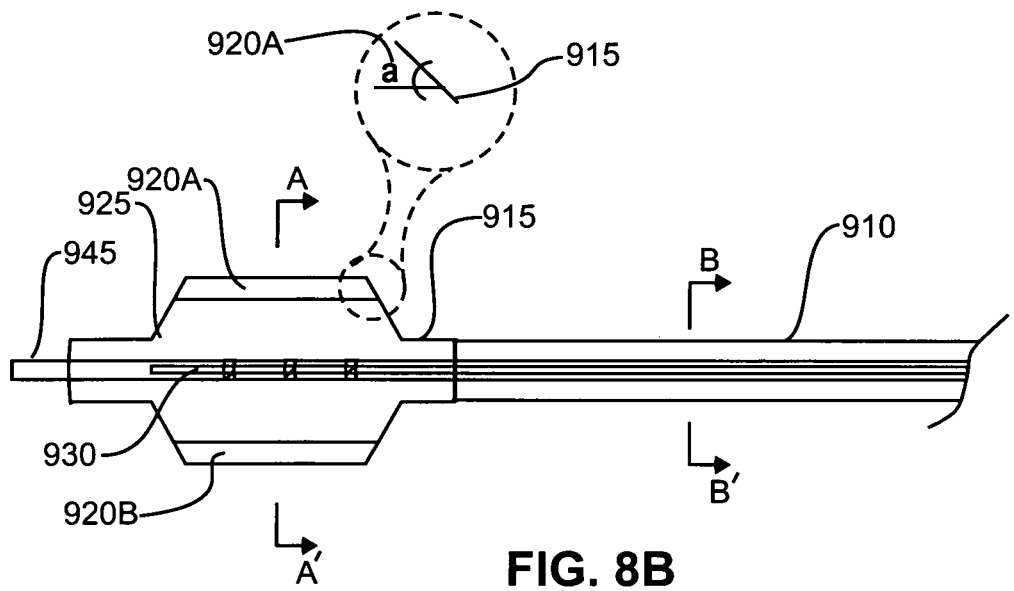
FIG. 8A
FIG. 8B

MAGNETIC RESONANCE IMAGING COILS

BACKGROUND

1. Field

Percutaneous coronary intervention devices.

2. Description of the Related Art

Medical catheters generally include elongated tube-like members that may be inserted into the body, either percutaneously or via a body orifice, for a wide variety of diagnostic and interventional purposes. Such catheters are particularly useful with regard to certain cardiovascular applications where an object is to deliver a treatment or instrument to a region of interest in a blood vessel (e.g., artery or vein) to modify (e.g., treat) a remote lesion.

Percutaneous Transluminal Coronary Angioplasty (PTCA or balloon angioplasty) and stenting are the predominant treatment for coronary vessel stenosis. In PTCA or stenting, a catheter is inserted into the cardiovascular system via, for example, a femoral artery. A pre-shaped guiding catheter is positioned in a coronary artery, and a dilatation catheter having a distensible balloon portion with or without a stent is advanced through the guiding catheter into the branches of the coronary artery until the balloon portion traverses or crosses a stenotic lesion. The balloon portion is then inflated with a medium to compress the lesion in a direction generally perpendicular to the wall of the artery, thus dilating the lumen of the artery. If a stent is also delivered with the balloon, it remains in the blood vessel and acts as scaffolding to hold the blood vessel open.

The position of a catheter in a vessel can be monitored using MRI techniques. Briefly, MRI is an imaging technique primarily used in medical settings to produce high-quality images of the internal human body. MRI is based on principles of Nuclear Magnetic Resonance (NMR), a spectroscopic technique used by scientists to obtain microscopic chemical and physical information about molecules.

Generally, the human body consists primarily of fat and water. Fat and water have many hydrogen atoms that make the human body approximately 63 percent hydrogen atoms. The nucleus of a hydrogen atom is comprised of a single proton. A property called "spin" is possessed by a single proton in a hydrogen atom. Spin can be thought of as a small magnetic field that causes the nucleus to produce an NMR signal.

During magnetic resonance imaging, a MRI system generates a strong magnetic field. When a target object (containing water molecules or other hydrogenous compounds) is positioned in the field, the field aligns magnetic dipoles of the hydrogen nuclei within the target object (and other hydrogen atoms). The magnetic field strength required to so align the magnetic dipoles is typically on the order of one Tesla, but field strengths significantly higher and lower than one Tesla are also used in various applications of MRI. The magnetic field imparts a resonant frequency to the nuclei that is proportional to the field strength. Once aligned by the magnetic field, the magnetic dipoles can be rotated out of alignment by application of radio frequency (RF) energy at the resonant frequency of the system. Electromagnetic radiation is subsequently emitted by the resonating magnetic dipoles (i.e., the protons spinning at their resonance frequency) as they return to alignment with the field. Imaging occurs as a result of detecting such radiation emitted from each of many different regions within the target.

Signal transmission and reception are produced through use of a radio frequency (RF) transmitter connected to a transmitting coil or antenna within the imaging unit (an "MR scanner") and a RF receiver connected to a "receiver coil" also located in the imaging unit. The receiving coil is positioned as close to the object as possible for maximum imaging sensitivity. The patient or object is often surrounded by a body coil that may serve both as transmitting and receiving antennae. Alternatively, the body coil can be used as a transmitting antenna only, and a separate surface coil is used as a receiving antenna. The surface coil can usually be placed closer to the tissues or object under examination than a single body coil. An RF oscillator generates radio waves of different frequencies. By controlling the magnetic field in a known way through a switching system that controls the current in the gradient coils, and by generating radio waves of a select frequency, the exact location at which the body of a patient or an object is imaged can be controlled. When the frequency of the RF signal is set for the exact value of the magnetic field, resonance occurs. Precession of the excited nuclear magnetic moment leads to induction of small currents in the receiving coil. The induced currents are detected to produce an output signal dependent upon the number of protons involved in the resonance and tissue-specific parameters. The output signal from the RF receiver is processed by a computer system to produce an image display of the tissue or the location of the RF receiver antenna.

While the ability to use MR imaging techniques to position a catheter to an area within the vasculature of a patient may be achieved with current technology, high resolution imaging of a targeted vascular site, such as stenosed vascular site is difficult to achieve. Recent research has indicated that in addition to a stenosed region of the vasculature, lesions referred to as thin-capped fibroatheromes (TCFAs) present a significant problem to cardiac function. TCFAs are lesions with large lipid pools, that are contained within the vessel wall by thin, fibrous caps. When a TCFA ruptures, a stenosed region may immediately form.

To diagnose TCFAs, current technology requires an imaging resolution of 50 to 100 microns. Current MR imaging techniques with a receiver coil placed external to a body of a patient do not provide adequate resolution to detect TCFAs. Obtaining a high resolution is complicated even in placing an RF antenna or coil in a blood vessel, because of blood vessel translation in response to cardiac pulsation and respiration; dilation/contraction of a blood vessel lumen and wall thickness in response to cardiac pulsation; and motion of the antenna or coil within a blood vessel due to hemodynamics.

SUMMARY

An apparatus suitable in one aspect for use in connection with imaging applications is described. In one embodiment, an apparatus includes a device such as a catheter or guidewire having dimensions suitable for percutaneous delivery to a patient, and a magnetic resonance (MR) compatible antenna associated with the device in a manner that provides at least one of a prescribed radial orientation and longitudinal orientation of the antenna at a point of interest within a blood vessel of a patient. A prescribed orientation includes centering an antenna in a blood vessel or locating an antenna adjacent the wall of the blood vessel. For example, the antenna may be positioned in a radial center of a region of interest within a blood vessel through assistance by a medical device such as a catheter, balloon dilation catheter, or guidewire. Alternatively, the antenna may include one or a number of conductive elements (antenna or coil elements) positioned in or around an interior of a blood vessel wall, with a device possibly maintaining the position of the conductive elements during an imaging procedure. The signal or signals is/are conveyed to signal processing equipment (e.g., an MR scanner) and converted to an image. By prescribing a radial orientation of an antenna, MR signal reception within a blood vessel may be improved and signal reception (e.g., uniform signal reception) of up to an entire circumference of, a blood vessel wall may be improved. In addition, a prescribed radial orientation of an antenna offers, in one embodiment, uniform signal reception of up to an entire circumference of a blood vessel wall. Further, a prescribed radial orientation will tend to reduce image artifacts caused by physiological motion of the blood vessel wall, such as occurs in pulsation. Various embodiments also describe an apparatus that will allow fluid (e.g., blood) perfusion during an imaging procedure.

An apparatus including a MR imaging antenna (possibly as a number of conductive elements (antenna elements) may also be used to actively track a device (e.g., catheter) through a body lumen, such as the vasculature. In this aspect, the MR imaging antenna serves as a device marker. Active tracking markers on a device can transmit signals to signal processing equipment (e.g., an MR scanner) and provide information on the location of the device. With this information, the signal processing equipment is used to guide a device to an appropriate scanning plane, for example, within a blood vessel, and can track the device plane-by-plane as it moves through the vasculature.

Various embodiments of antenna structures are presented. Embodiments include, but are not limited to, general classifications of cage (e.g., "bird cage") configurations of multiple conductive elements; configurations of multiple connected and/or unconnected longitudinally disposed conductive elements; opposed solenoid configurations; cage configurations of multiple conductive elements with or without supporting elements; spiral configurations of multiple conductive elements; and dipole configurations.

Various device platforms are presented. One device platform includes expandable structures. For example, embodiments describe an antenna made from or mounted on/in a cage of, for example, a conductive metallic material, possibly a shape memory material. In one example, the cage is deployed at a region of interest within a blood vessel in a collapsed state, then deployed to a position against or in close proximity to a blood vessel wall. As a configuration of an antenna(e) of multiple conductive elements, the antenna may be expanded at a region of interest to place the conductive elements against or in close proximity to a blood vessel wall. An antenna(e) of multiple conductive elements may alternatively be placed within, deposited on or mounted on an outer or inner surface of a device, such as a balloon of a balloon catheter or similar device. In such case, the balloon may be used to expand the antenna(e) against or in close proximity to an inner surface of a blood vessel wall. In another example, the antenna is mounted or encapsulated in expandable polymeric or MR compatible metallic (e.g., low magnetic susceptibility cages). Compressing the cage(s) along a longitudinal axis expands the cage(s).

A second device platform includes devices that may be used to axially align (e.g., center) antenna structures (e.g., dipole and opposed solenoid antennae) in the lumen of a blood vessel. To axially center an antenna that, for example, extends along a longitudinal axis of the device and has an unexpandable diameter, suitable centering devices include devices with one or several balloon portions; a plurality of cannulas (tubes) mounted on the outer surface of a balloon portion; and one or several expandable (including compression expandable) polymer or MR-compatible metal cages.

One application for embodiments of the apparatus described herein is the imaging of blood vessel walls or nearby tissue. Also disclosed herein is a method including inserting a medical device having an antenna capable of transmitting radio frequency signals in a blood vessel of a patient and radially orienting the antenna at a point of interest within a blood vessel of a patient. Radio frequency signals include those resulting from MR scanning equipment that may be received and transmitted by the antenna to form an image of the blood vessel walls. One method provides a technique to diagnose abnormalities, such as thin-capped fibroatheromas (TCFAs). A suitable resolution on the order of 50 to 100 microns may be achieved if the antenna is placed close to the region of interest such as in the radial center of a blood vessel or adjacent a wall of the blood vessel.

In addition to vascular applications, the devices and methods described herein can be used to image various tissues within a body cavity.

BRIEF DESCRIPTION OF THE DRAWINGS

FIG. 1 illustrates an embodiment of a portion of an imaging device including a number of magnetic resonance (MR) radio frequency (RF) conductive elements in a cylindrical, axially-aligned "bird-cage" coil.

FIG. 1A illustrates a catheter assembly with a sheath constraining the coil from FIG. 1 in a collapsed configuration.

FIG. 1B illustrates the catheter assembly of FIG. 1A after a sheath is retracted exposing the coil.

FIG. 2A illustrates another embodiment of a portion of an imaging device including a number of magnetic resonance RF conductive elements in a cylindrical, axially-aligned "bird-cage" coil.

FIG. 3A illustrates an embodiment of a catheter assembly including a balloon catheter, having a MR compatible balloon portion with an antenna connected to the balloon portion.

FIG. 3B shows a cross-sectional view of the catheter assembly of FIG. 3A through line A-A'.

FIG. 3C shows a cross-sectional view of the catheter assembly of FIG. 3A through line B-B'.

FIG. 4A illustrates an embodiment of a catheter assembly including a balloon catheter having an MR compatible balloon portion with an antenna connected to the balloon portion.

FIG. 4B shows a cross-sectional view of the catheter assembly of FIG. 4A through line A-A'.

FIG. 4C shows a cross-sectional view of catheter assembly of FIG. 4A through line B-B'.

FIG. 4D shows a cross-sectional view of another embodiment of the catheter assembly of FIG. 4A through line A-A'.

FIG. 5A illustrates an embodiment of a catheter assembly including a balloon catheter having an MR compatible balloon portion with an antenna connected to the balloon portion.

FIG. 5B shows a cross-sectional view of the catheter assembly of FIG. 5A through line A-A'.

FIG. 5C shows a cross-sectional view of the catheter assembly of FIG. 5A through line B-B'.

FIG. 5D shows a cross-sectional view of the catheter assembly in FIG. 5A through line C-C'.

FIG. 6A illustrates an embodiment of a catheter assembly including a balloon catheter having an MR compatible balloon portion with an antenna coaxially aligned with the balloon catheter.

FIG. 6B shows a cross-sectional view of the catheter assembly of FIG. 6A through line A-A'.

FIG. 6C shows a cross-sectional view of the catheter assembly of FIG. 6A through line B-B'.

FIG. 8A illustrates another embodiment of a catheter assembly including a coaxial shaft including a balloon catheter and an antenna aligned with the shaft.

FIG. 8B shows the catheter assembly of FIG. 8A with a balloon portion of the balloon catheter in an inflated state.

DETAILED DESCRIPTION

Figure 2B:
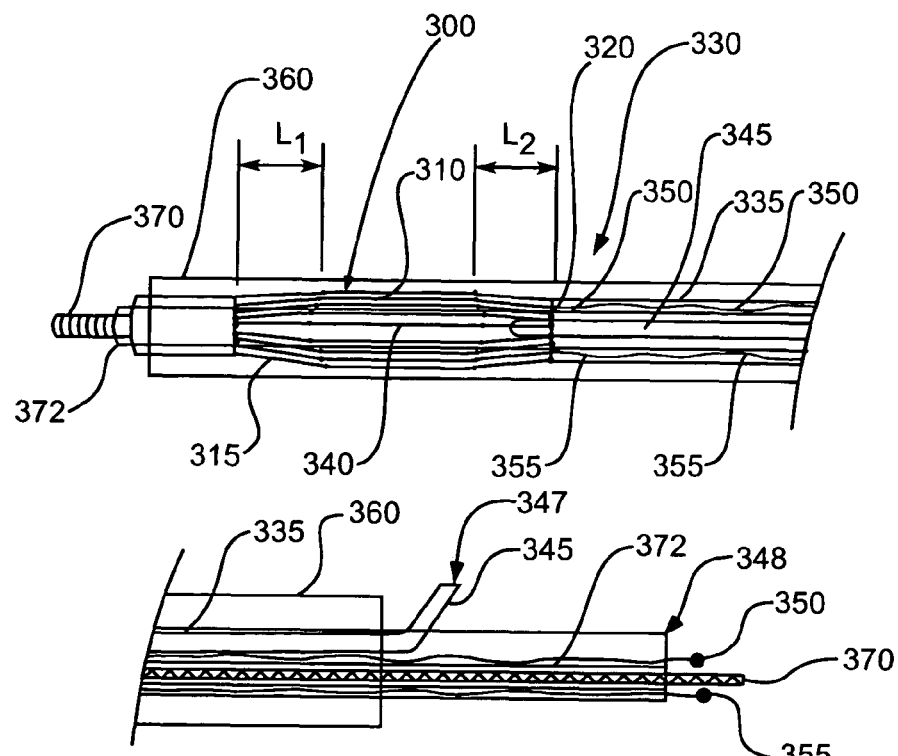
FIG. 2B illustrates a catheter assembly including a coil such as the coil of FIG. 2A is connected to or disposed on a balloon catheter.

Embodiments suitable for magnetic resonance (MR) imaging that, in one embodiment, may enhance visualization of percutaneous coronary intervention (PCI) or surgical or other devices are described. Referring to the figures, exemplary embodiments of various apparatuses and methods will now be described. The exemplary embodiments are provided for illustration and should not be construed as limiting the scope of any claimed subject matter.

FIG. 1 illustrates an embodiment of a portion of an imaging device including a number of magnetic resonance (MR) radio frequency (RF) conductive elements (antennas or coils) in a cylindrical, axially-aligned "bird-cage". In one embodiment, coil 100 includes first connecting portion 120 and second connecting portion 125, illustrated, in this embodiment as elliptical (e.g., circular) portions. It is appreciated that other shapes may also be suitable.

Positioned between first connecting portion 120 and second connecting portion 125 are a number of conductive elements 110 that are suitable for magnetic resonance (MR) imaging. In one embodiment, conductive elements 110 are one or more antennas or receiver coils that receive radio frequency (RF) signals or induction currents from tissue (e.g., a wall of a blood vessel) in response to RF from an oscillator (an MR scanner) external to the patient. Conductive elements 110 are connected to tuning and/or matching or other circuitry positioned within a catheter used to locate a device including coil 100 or external to such a catheter (e.g., external to a blood vessel or vessels through which a PCI device is inserted). Conductive elements 110 may transmit the received signals to the imaging circuitry. Conductive elements 110 may be used to position coil 100 at a region of interest within a blood vessel or to image the blood vessel during deployment. In this manner, conductive elements serve as tracking elements (antennas) that transmit signals to signal processing equipment and provide information on the location of the device as well as images of a blood vessel, or other cavity during deployment. Alternatively, conductive elements may be deployed at a predetermined region of interest within a blood vessel and provide an image, possibly of an entire blood vessel wall, at the region of interest.

The number of conductive elements 110 may be proportional, based on the size (e.g., diameter) of coil 100 (e.g., the larger the coil, the more conductive elements 100). The number of conductive elements, in one embodiment, is maximized, given the available diameter of, for example, a blood vessel within a vasculature of a patient. For example, a coil such as coil 100 suitable for positioning adjacent to (e.g., against) a blood vessel with a diameter on the order of three millimeters (3 mm) may have four conductive elements each having a cross-sectional diameter on the order of 0.002-0.003 inches and longitudinally arranged in a cylindrical configuration and laterally spaced by approximately 90°.

In one embodiment, alternating conductive elements 110 of coil 100 receive radio frequency (RF) signals. In one embodiment, each of the number of conductive elements 110 are connected to one another, through first connecting portion 120 and second connecting portion 125. Alternatively, pairs or other groups of conductive elements 110 may be connected. Pairs of conductive elements 110 may act as a dipole. Pairs of conductive elements 110 may be in a phase relationship, such as a quadrature relationship (e.g., separated in phase by)90°.

Conductive elements 110, in one embodiment, are made of a material capable of conducting an RF signal. Representative metal materials include, but are not limited to copper, aluminum, gold, titanium, tantalum, platinum, brass, silver, and various alloys including but not limited to nickel-titanium alloy (nitinol). Conductive elements 110 may be coated with an insulation material. Conductive elements 110 may be made form tubing (e.g., machined or cut) or may be wires or ribbons.

In another embodiment, coil 100 may include less conductive (e.g., less susceptible to receive MR frequency signals) or non-conductive or MR compatible elements in addition to conductive elements 110. Representatively, less-conductive or non-conductive elements may be used as support structures for the coil or antenna structure. In another embodiment, first connecting portion 120 and second connecting portion 125 may be made of MR conductive materials or may be made of non-conductive or MR compatible materials.

In one embodiment, coil 100 is selected to have a diameter, in an expanded configuration, approximately equivalent to an interior diameter of a blood vessel wall at a region of interest. Coil 100 is inserted into an anatomy (e.g., a vasculature of a patient) in a collapsed state, such as on the exterior of a balloon of a balloon catheter. One way coil 100 may be collapsed is through the use of discontinuous segments 128 that collectively form each of connecting portion 120 and second connecting portion 125 (e.g., each segment connected to respective pairs of conductive elements 110). In a collapsed state, the segments collapse such that the distance between respective conductive elements 110 is minimized. Once coil 100 reaches the region of interest in the anatomy, coil 100 is expanded, for example, by expanding a balloon. The expansion of a balloon tends to increase a diameter of coil 100 by increasing the distance between conductive elements 110. In one embodiment, at a maximum distance of respective conductive elements 110 between segments 128, the exterior of the plurality of conductive elements 110 are adjacent to or in contact with a vessel wall within an anatomy.

In another embodiment, coil 100 is made from a material that will expand from a first collapsed cylindrical configuration having a first diameter suitable for being advanced through a blood vessel (e.g., artery, vein, etc.) on the exterior of a shuttle PCI medical device, such as a guidewire (e.g., an outer diameter on the order of 0.01-0.04 inches) or deflated balloon, to a second expanded diameter similar to the interior diameter of a blood vessel. One suitable material is a material having shape memory, such as a nickel titanium alloy (e.g., nitinol). The material is referred to as having a shape memory, with the shape that is remembered being the expanded shape brought about by the conditions (e.g., fluid, heat) to which coil 100 is exposed. In one embodiment, to inhibit the expansion of the size of a shape memory material until coil 100 is at or near a region of interest, the shuttle medical device including coil 100 is encompassed within a sheath. At the region of interest, the sheath is retracted to expose coil 100 to an environment in which the material of coil 100 will be modified. In one embodiment, a nitinol material may have a core, such as copper, that is more conductive (e.g., more receptive to MR frequency signals) than the nitinol material.

FIG. 1A illustrates a catheter assembly including coil 100. Catheter assembly 200 includes balloon catheter 201, with coil 100 mounted on balloon portion 203 at a distal portion of the catheter. Overlying balloon catheter is sheath 205. Additional lumens may be placed within or exterior to sheath 205. Such additional lumens may be used, for example, for transmitting fluid (e.g., a treatment agent) or an additional imaging device through catheter assembly 200.

Balloon portion 203 in this figure is deflated. Balloon catheter 201, including balloon portion 203 may be made of MR-compatible material (e.g., materials with no or relatively low magnetic susceptibility that will not be attracted to the relatively strong magnetic field of an MR scanner or excessively distort a received image). For the various embodiments described herein, MR compatible material includes polymers such as polyether block amides (e.g., PEBAX®, polyetheretherketone (PEEK), braided nylon, or other MR compatible polymers). "Polymer," "poly," and "polymeric" are herein defined as compounds that are the product of a polymerization reaction, combination or addition and are inclusive of homopolymers, copolymers, terpolymers etc., including random, alternating, block, and graft variations thereof. Representative examples of polymers that can be used as with or as part of an MR compatible material various embodiments described herein include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(etheresters) (e.g. PEO/PLA); polyalkylene oxalates; polyphosphazenes and biomolecules such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters; such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides; such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

In addition to polymers, other MR compatible materials include non-ferromagnetic metal materials or metal materials that may, for example, be interpreted and displayed as voids on imaging circuitry, including but not limited to, copper, aluminum, gold, nitinol, titanium, tantalum, platinum, brass, and silver.

Referring to FIG. 1A, coil 100 is connected to tuning and/or matching or other circuitry by leads 210 and 215 shown, in this example, on the exterior of balloon catheter 201 (within sheath 205). Leads 210 and 215 may extend to circuitry located within catheter assembly 200 internal to a body (vasculature) in which catheter assembly 200 is inserted or external to the body (e.g., at a proximal end of catheter assembly 200).

To place catheter assembly 200 at a region of interest within a blood vessel, balloon catheter 201 may have a number of passive markers 150. Passive markers 150 are a material that may be detected by MR circuitry as, for example, voids in a received image. Suitable materials for passive markers 150 include materials such as tantalum, titanium, gold, platinum, nitinol or other materials as bands (such as flat wire bands) that may be positioned on balloon catheter 201. Balloon catheter 201 may be advanced over a previously introduced guidewire until balloon portion 203 is positioned at a region of interest.

FIG. 1B illustrates catheter assembly 200 after sheath 205 is retracted exposing coil 100. Balloon portion 203 of balloon catheter 201 is inflated with, for example, a suitable fluid introduced through a proximal end of balloon catheter 201 (e.g., through a designated inflation port and lumen). The expansion of balloon portion 203 causes coil 100 to expand from a first diameter to a larger second diameter, in one embodiment, approximating the inner diameter of a blood vessel. Once coil 100 is expanded, coil 100 may be used to transmit imaging signals about the blood vessel wall or surrounding tissue. Coil 100 may alternatively expand (e.g., without the need, for example, of an inflated balloon) because it is a shape memory material such as nitinol. In such case, coil 100 is deployed in a protected state (e.g., protected by an overlying sheath) and then unprotected at a region of interest.

FIG. 2A illustrates another embodiment of a portion of an imaging device including a number of magnetic RF conductive elements in a cylindrical, axially-aligned "bird-cage" coil. It is appreciated that the coil, either in a collapsed or expanded state, need not have a cylindrical configuration. In this embodiment, coil 300 is sized to be advanced to a region of interest by a medical device, such as connected to a guidewire or connected to or disposed on a balloon portion of a balloon catheter.

In one embodiment, coil 300 includes first connecting portion 320 and second connecting portion 325. First connecting portion 320 and second connecting portion have, for example, a circular lateral cross-section with a diameter selected to fit on (over) a PCI device such as a guidewire or catheter. Disposed between first connecting portion 320 and second connecting portion 325 are conductive elements 310. In one embodiment, conductive elements 310 are connected to one another or in pairs (e.g., dipoles) or in groups in a phase relationship (e.g., quadrature) for signal reception. It is appreciated that each of conductive elements need not be conductive (e.g., capable of transmitting a MR frequency signal). Connected between first connecting portion 320 and second connecting portion 325 and conductive elements 310 are segments 315. When coil 300 is in a collapsed (unexpanded) advancing configuration, segments 315 are generally axially aligned with conductive elements 310, thus minimizing the diameter of coil 300. When coil 300 is in an expanded configuration, segments 315 adopt, in one example, a generally conical shape with an apex at a proximal end (first connecting portion 320) and a distal end (second connecting portion 325), respectively. Coil 300 is inserted/advanced into an anatomy in a collapsed state. Once coil 300 reaches a region of interest in an anatomy (e.g., in a vasculature), coil 300 may be expanded so that the exterior of the plurality of conductive elements 310 are adjacent to or in contact with a vessel wall within an anatomy.

FIG. 2B illustrates a catheter assembly including a coil such as coil 300 connected to or disposed on a balloon catheter. Catheter assembly 330 includes balloon catheter 335 including balloon portion 340 at a distal portion of balloon catheter 335. Balloon portion 340 is filled through cannula 345 at inflation port 347 at a proximal end of catheter assembly 330. Coil 300 is connected to or disposed on balloon portion 340. Conductive elements 310 have a length in one embodiment, similar to a working length of balloon portion (e.g. 5-50 mm). Conductive leads 350 and 355 are connected to conductive elements 310 through a proximal end of coil 300 (at first connecting portion 320) and extend, in this embodiment, external to balloon catheter 335 through a proximal end of balloon catheter 335 to circuitry external to catheter assembly 330. In one embodiment, conductive leads 350 and 355 represent signal lines to transmit MR imaging signals from coil 300 to MR imaging circuitry external to catheter assembly 300. Conductive leads 350 and 355 are shown, in this embodiment, extending at a proximal end through entry port 348. It is appreciated that there may be more or less than two leads.

As illustrated in FIG. 2B, in a collapsed state, coil 300 has, in this embodiment, a generally cylindrical shape. Catheter assembly 330 has a size (diameter) suitable for insertion into a blood vessel such as a coronary artery. For insertion purposes, sheath 360 may optionally be disposed over/on balloon catheter 335 and coil 300. Catheter assembly 330 may be advanced to a region of interest by guidewire 370. In one embodiment, guidewire 370 extends the length of catheter assembly 330 through cannula 372 to entry point 348 at a proximal end of catheter assembly 330. Representatively, guidewire 370 is initially placed through the region of interest and balloon catheter 335 is advanced on/over guidewire 370 to the region of interest in an over the wire (OTW) fashion. In another embodiment, balloon catheter 335 of catheter assembly 330 is a rapid transfer catheter and only a portion of balloon catheter 335 (a distal portion) is advanced over guidewire 370. Guidewire 370 may be retracted or removed once catheter assembly 330 is placed at a region of interest.

Referring to FIG. 2B, coil 300 is in a collapsed state on balloon portion 340 of balloon catheter 335. Conductive portions 310 and segments 315 are approximately or actually axially aligned with balloon catheter 335. Segments 315 form cylindrical bodies having a length, $L_1$, of approximately two to 10 millimeters (mm), in one embodiment, corresponding with transition or tapered portions of balloon portion 340.

Figure 2C:
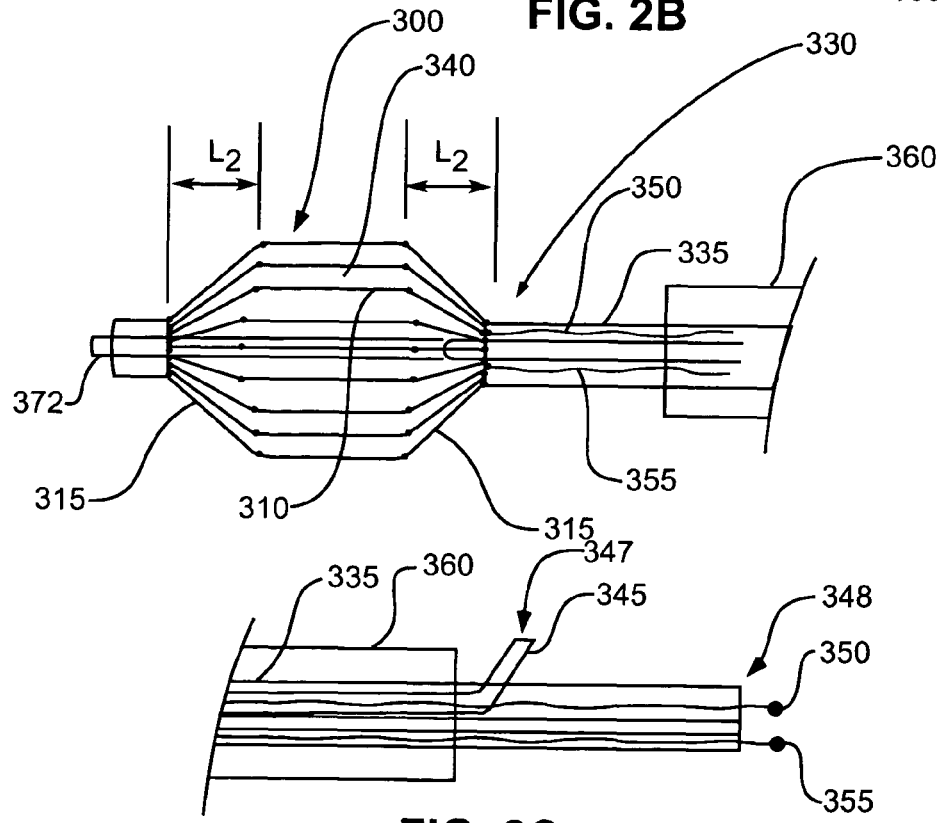
FIG. 2C shows the catheter assembly of FIG. 2B with a balloon portion of a balloon catheter in an inflated state.

FIG. 2C shows catheter assembly 330 with balloon portion 340 of balloon catheter 335 in an inflated (expanded) state.

Balloon portion 340 may be inflated by introducing a suitable liquid through cannula 345 (at inflation port 347) to expand (inflate) balloon portion 340 to a desired size, such as a diameter corresponding to an internal diameter (or slightly less than an internal diameter) of a blood vessel of the region of interest. Inflation of balloon portion 340 expands the diameter of coil 300 so that, in one embodiment, conductive members 310 are adjacent to or against the wall of a blood vessel at the region of interest. In such an event, segments 315 adopt a collective conical shape with a base having a diameter similar to a diameter of expanded balloon portion 340 at its largest point and an apex having a diameter similar to a diameter of balloon catheter 335 without balloon portion 340. A length, $L_2$, of the collective conical shaped segments is less than a length $L_1$ (see FIG. 2A).

Once coil 300 is expanded, balloon catheter 335 may be removed from the blood vessel or retained at or retracted from the region of interest by deflating balloon portion 340 to a collapsed state. Once balloon portion 340 is deflated, balloon catheter 335 may be retained at or retracted from the region of interest leaving coil 300 at a region of interest. Segments 315 of coil 300 may include locking mechanisms to retain coil 300 in an expanded state within the blood vessel. Suitable locking mechanisms include barbs on segments 315 and/or conductive elements 310.

Figure 2D:
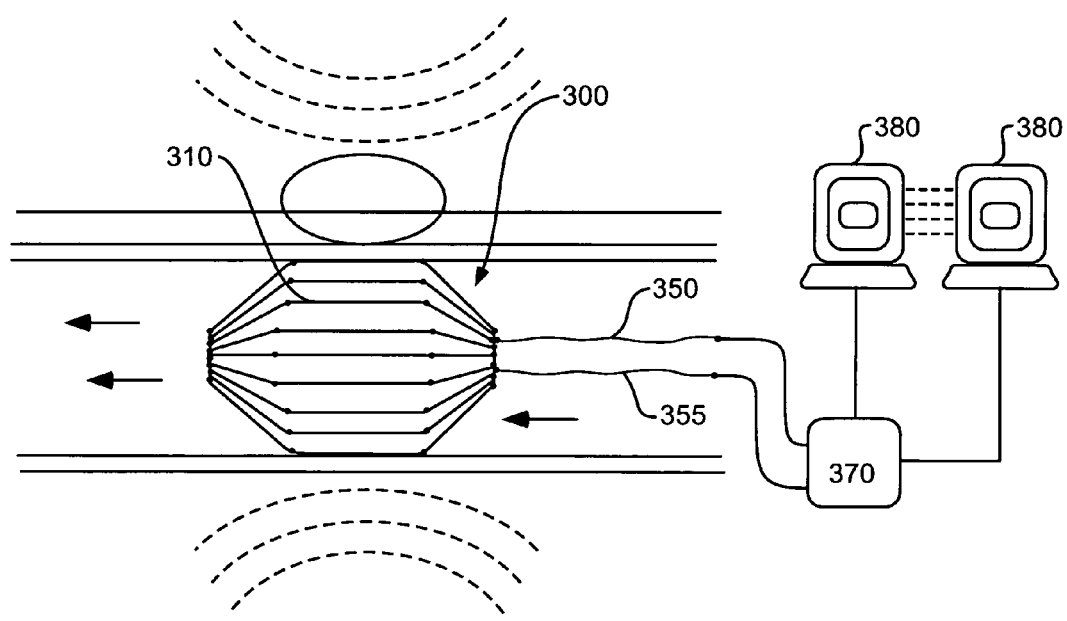
FIG. 2D shows the coil of FIG. 2A in an expanded state or configuration adjacent a wall of a blood vessel and receiving and transmitting RF signals.

FIG. 2D shows coil 300 within a blood vessel. Conductive elements 310 may receive RF signals produced by a MR scanner external to the anatomy of a patient. The received signals may be transmitted from conductive elements 310 through leads (e.g., conductive leads) 350 and 355 to MR processing circuitry 370. MR processing circuitry 370 may then be used to produce (image) the received signals on monitor 380. In one embodiment, leads 350 and 355 transmit two different signals. The signals represent two different views of a region of interest, such as a wall of a blood vessel. FIG. 2D shows two separate, possibly sequential, images on monitor 380 (e.g., one image orthogonal to the other).

FIG. 3A illustrates another embodiment of a catheter assembly, including a balloon catheter, having a MR compatible balloon portion. In this embodiment, catheter assembly 400 includes balloon catheter 410 including balloon portion 415. Balloon portion 415 includes stripes 420 on the exterior of balloon portion 415. In one embodiment, stripes 420 are conductive elements of, for example, a conductive material. One way to form stripes 420 is by a deposition process of conductive material on balloon portion 415. One suitable deposition process is a chemical vapor deposition (CVD) of an elastomeric metal material onto balloon portion 415. In such a process, a portion of balloon portion 415 is masked or protected with a suitable masking material and stripes of balloon portion 415 are left exposed. Conductive material may then be deposited on the exposed stripes. The masking material may then be removed leaving only MR compatible stripes 420 on balloon portion 415. The deposited conductive material may be connected to leads external to or within balloon catheter 410. In another embodiment, stripes 420 are wires or ribbons that are connected (e.g., glued) in a longitudinal arrangement to an exterior surface of balloon portion 415. In either embodiment, stripes 420 may be connected to conductive leads that extend toward a proximal end of catheter assembly 400 (leads not shown).

In another embodiment, conductive material stripes are disposed within respective cannula or tubing connected to the surface of a balloon portion of a balloon catheter. FIG. 3B shows a cross-section through line A-A' of FIG. 3A. FIG. 3B shows stripes 420 including conductive material 430 disposed within cannula 425. Cannula 425 is for example a polymeric material (e.g., elastomeric polymer tubing) having a longitudinal length similar to a working length of balloon portion 415 and a lumen with an interior diameter large enough to accommodate an exterior dimension (e.g., diameter) of conductive material 430. Conductive material 430 is for example a metal wire or ribbon.

FIG. 3B shows a cross-sectional view of balloon portion 415 of catheter assembly 400 through line A-A'. Balloon portion 415 is shown in an expanded (inflated) state or condition. In a blood vessel, balloon portion 415 may be expanded to be adjacent to an interior wall of a blood vessel. Stripes 420 are located circumferentially around the elliptical (e.g., circular) cross-section of balloon portion 415. Balloon portion 415 may be expanded so that stripes 420 contact an interior wall of the blood vessel. The number of stripes 420 may be selected so as to maximize the MR imaging capabilities of catheter assembly 400 and allow sufficient fluid (e.g., blood) perfusion beyond balloon portion 415, for example, through spaces or gaps between adjacent stripes 420.

FIG. 3B also shows cannula 440 disposed within balloon portion 415. Cannula 440, in one embodiment, extends from a proximal end to a distal end of balloon catheter 410 through a lumen of balloon catheter 410 (see FIG. 3A). Cannula 440 may have a lumen therethrough suitable for accommodating a guidewire so that catheter assembly may be advanced over a guidewire to a region of interest.

In one embodiment, cannula 440 and balloon catheter 410, including balloon portion 415 are made of MR compatible material similar to suitable materials described in previous embodiments. Balloon catheter 410 or cannula 440 may have a number of passive markers (e.g., MR passive markers) along a distal portion to position balloon portion 415 at a region of interest.

FIG. 3C illustrates a cross-sectional view of the embodiment of catheter assembly 400 illustrated in FIG. 3A through line B-B'. From this view, balloon catheter 410 includes cannula 450 providing an inflation lumen for balloon portion 415. Cannula 450 extends from a proximal end of catheter 410 (at entry port 455 (see FIG. 3A)) to balloon portion 415. A suitable fluid may be introduced at inflation port 455 to inflate balloon portion 415. FIG. 3C also shows cannula 440 having a lumen therethrough of a size suitable for a guidewire. Catheter assembly 400 may be advanced over guidewire through entry port 475. (See FIG. 3A.)

Referring to FIG. 3C, disposed within cannula 450 (the inflation lumen for balloon portion 445) is circuitry 460. Circuitry 460 may constitute a lead (e.g., cable) extending through the inflation lumen to MR circuitry external to catheter 400. Alternatively, circuitry 460 may include circuit components disposed within the inflation lumen. Representatively, circuitry 460 may include a tuning capacitor. Circuitry 460 is connected to conductive elements 430 of stripes 420 (see FIG. 3B). Conductive elements 430 extend from balloon portion 415 through, in one embodiment, cannula 450 to circuitry 460. Circuitry 460 extends through entry port 465 where it may be connected to additional MR circuitry external to catheter assembly 400.

FIG. 4A illustrates another embodiment of a catheter assembly including a balloon catheter having a MR compatible balloon portion. In this embodiment, catheter assembly 500 includes balloon catheter 510 including balloon portion 515. Balloon portion 515 includes a number of stripes 520 formed in longitudinal channels in a wall of the material that forms balloon portion 515.

FIG. 4B shows a cross-section through line A-A' of FIG. 4A. FIG. 4B shows balloon portion 515 having a number of channels 525 disposed longitudinally around balloon portion 515. Disposed within respective channels 525, in this embodiment, are conductive elements 530 of, for example, a wire or ribbon. Thus, channels 525 have an interior diameter large enough to accommodate an exterior dimension (e.g., diameter) of individual conductive elements 530. Channels 525, in one embodiment, have a longitudinal length similar to a working length, L of balloon portion 515 (see FIG. 4A). At a proximal end of balloon portion 515, conductive elements 530 in each of the individual channels 525 may connect individually, collectively, or in pairs or other groups, to MR circuitry extending through a portion of balloon catheter 510.

FIG. 4B shows balloon portion 515 in an expanded (inflated) state or condition. In a blood vessel, balloon portion may be expanded to be adjacent to an interior wall of the blood vessel. Thus, the individual conductive elements 530 in channels 525 in the wall of balloon portion 515 will be adjacent the wall of the blood vessel. The number of stripes 520 including conductive elements 530 may be selected so as to maximize the MR imaging capabilities of catheter assembly 500.

One way channels 525 may be formed in balloon portion 515 is through an extrusion process where channels or grooves are formed as a balloon portion is extruded through a die. Conductive elements 530 may then be added to channels 525 and a suitable polymer or other insulative coating may be formed over the channel to encapsulate individual conductive elements 530. In another embodiment, illustrated in FIG. 4D, multiple channels may be formed in balloon portion 515 and only a portion of the channels include conductive elements 530 and are encapsulated. The remaining channels 575 are left intact to allow fluid (e.g., blood) perfusion by balloon portion 515.

Referring again to FIG. 4B, cannula 540 is shown disposed within balloon portion 515. Cannula 540, in one embodiment, is a guidewire cannula, extending, in this example, from a proximal to a distal end of balloon catheter 510 (see FIG. 4A). In one embodiment, catheter assembly 500 may be introduced over guidewire 545 through port 575.

FIG. 4C illustrates a cross-sectional view of the embodiment of catheter assembly 500 illustrated in FIG. 4A through line B-B'. From this view, balloon catheter 510 includes cannula 550 providing an inflation lumen for balloon portion 545. Cannula 550 extends from a proximal end of balloon catheter 510 (at inflation port 555) to balloon portion 515. A suitable fluid may be introduced at inflation port 555 to inflate balloon portion 515. FIG. 4C also shows cannula 540 that has a lumen therethrough suitable for a guidewire. In one embodiment, lumen 540 extends the length of the catheter from a distal end of balloon portion 515 to a proximal end defined by port 575 (see FIG. 4A).

FIG. 4C shows circuitry 560 disposed within the lumen of cannula 550 (within the inflation lumen). Circuitry 560 may include a lead or cable connected at a distal end to one or more conductive elements 530 at a proximal end of balloon portion 515. Such a lead or cable may extend through entry port 565 (see FIG. 4A) to connect to MR circuitry external to catheter assembly 500. Alternatively, circuitry 560 may include additional component circuitry, including a tuning capacitor within the inflation lumen.

FIG. 4D illustrates a cross-sectional view of another embodiment of catheter assembly 500. From this view, balloon catheter 510 is shown having a number of channels 525 disposed longitudinally around balloon portion 515. Disposed within respective channels 525, in this embodiment, are conductive elements 530 of, for example, a wire or ribbon. Thus, channels 525 have an interior diameter large enough to accommodate an exterior dimension (e.g., diameter) of individual conductive elements 530. In this manner, the embodiment of balloon 515 and conductive elements 530 are similar to that described with reference to the embodiment illustrated in FIG. 4B. In addition, balloon 515, in this embodiments, includes a plurality of secondary channels 575 disposed longitudinally around balloon portion 515. In one embodiment, secondary channels 575 extend a length similar to a working length of balloon 515. In this manner, secondary channels 575 provide an area (volume) for blood perfusion beyond balloon 515 when balloon is inflated in a blood vessel (e.g., to contact a wall of a blood vessel).

FIG. 5A illustrates another embodiment of a catheter assembly including a balloon catheter having an MR compatible balloon portion. In this embodiment, catheter assembly 600 includes balloon catheter 610 including balloon portion 615. Balloon portion 615 includes multiple longitudinal lobes. FIG. 5B is a cross-sectional view through line A-A' of FIG. 5A. FIG. 5B shows balloon portion 615 having multiple lobes or fluted portions 620 formed around center cannula portion 625. FIG. 5B shows a multi-lobed balloon portion having three lobes (lobe 620A, lobe 620B, and lobe 620C). It is appreciated that in other embodiments, a multi-lobed balloon may include a different number of lobes, such as for example, two, four, and five lobes. One way to form a multi-lobed balloon is through an extrusion process with a die having a head with a multi-lobed shape. Lobes 620 include distal and proximal ends having a tapered configuration.

Referring to FIG. 5B, individual conductive elements 630 (e.g., 630A, 630B, and 630C) are disposed in respective inflation lumens of multi-lobed balloon portion 620. Conductive elements 630 are, for example, a wire, coil, or ribbon bonded to a wall of an individual lobe (lobe 620A, lobe 620B, and lobe 620C, respectively), with one or more conductive elements optionally connected to one another between lobes (e.g., as a dipole or in a phase relationship).

FIG. 5B shows cannula 640 extending through a central portion of balloon portion 615 (through center cannula portion 625). Cannula 640 includes a lumen suitable for accommodating a guidewire. Cannula 640, in this example, extends through a distal end of balloon portion 615. Cannula 640 is, in one embodiment, axially aligned with central cannula portion 625. Cannula 640 may include a number of passive markers that may be used to locate catheter assembly 600. Suitable passive markers include, but are not limited to, MR compatible flat wire bands (e.g., 0.005 inches by 0.002 inches) of titanium, tantalum, etc. bonded to cannula 640.

FIG. 5B shows balloon portion 615 in an expanded (inflated) state or condition. In a blood vessel, balloon portion 615 may be expanded to be adjacent to an interior wall of a blood vessel. Lobe 620A, lobe 620B, and lobe 620C are located circumferentially around the elliptical (e.g., circular) cross-section of center cannula 625. Balloon portion 615 may be expanded so that lobes 620 contact an interior wall of the blood vessel. The number of lobes may be selected so as to maximize the MR imaging capabilities of catheter 600 and allow sufficient fluid (e.g., blood) perfusion beyond balloon portion 615, for example, through spaces or gaps between adjacent lobes.

FIG. 5C shows a cross-sectional view of an embodiment of catheter assembly 600 illustrated in FIG. 5A through line B-B'. From this view, balloon catheter 610 includes cannula 650 providing an inflation lumen for balloon portion 615. Cannula 650 extends from a proximal end of balloon catheter 610 (at inflation port 655 (see FIG. 5A)) to balloon portion 615. A suitable fluid may be introduced at entry port 655 to inflate balloon portion 615. FIG. 5C also shows cannula 640 having a lumen with a dimension suitable for advancing catheter assembly 600 over a guidewire. Referring to FIG. 5A, cannula 640 does not extend to the proximal end of balloon catheter 610, but instead terminates at a medial portion with entry port 675 to illustrate a rapid transfer design. FIG. 5C also shows circuitry 660 disposed within cannula 650 (within the inflation lumen). Circuitry 660 may be a lead or cable extending at a proximal end to additional MR circuitry located external to balloon catheter 610 of catheter assembly 600. For example, a cable as circuitry 660 may extend through entry port 655 at a proximal end of balloon catheter 610. Alternatively, circuitry 660 may include additional MR circuitry, such as a tuning capacitor disposed (and possibly insulated) within the inflation lumen. FIG. 5D illustrates a cross-sectional view of the embodiment of catheter assembly 600 illustrated in FIG. 5A through line C-C'. From this view, cannula 650 is shown having a lumen therein (an inflation lumen). Circuitry 660 is disposed within the inflation lumen.

In the above embodiment, a multi-lobed balloon portion is described with individual conductive elements in each lobe. It is appreciated that each individual lobe may be inflated at once or individually. One way to individually inflate specific lobes is through individual cannulas (and lumens therethrough) extending from a manifold at the proximal end of balloon catheter 610 (e.g., at entry port 665), through balloon catheter 610 to balloon portion 615.

FIGS. 6A-6C illustrate another embodiment of a catheter assembly including a balloon catheter for use in MR imaging. In this embodiment, catheter assembly 700 includes balloon catheter 710 including balloon portion 715. Balloon portion 715 is a multi-lobed or fluted balloon. Disposed through a lumen of balloon catheter 710, including through balloon portion 715 of balloon catheter 710, is cannula 745. Balloon catheter 710 and cannula 745 are each made of MR compatible materials such as PEEK or braided nylon. Balloon portion 715 of balloon catheter 710 is also a MR compatible material such as PEBAX. Balloon portion 715 may be bonded to balloon catheter 710. Cannula 745 is, for example, suitable for a guidewire over which catheter assembly 700 may be advanced. Once catheter assembly 700 is placed, a guidewire may be removed from cannula 745 and replaced with conductive element 730 that is, for example, an MR receiver element (e.g., antenna or coil). Alternatively, the guidewire may serve two functions: to provide a guide for balloon catheter 710 and as an MR receiving element (e.g., antenna or coil). One example where such a dual purpose guidewire may be used is, for example, a rapid transfer type catheter design. FIG. 6A shows conductive element 730 inserted through cannula 745 so that a distal portion is located within balloon portion 715 of balloon catheter 710. FIG. 6A also shows catheter assembly 700 including sheath 705 that may optionally be disposed on/over balloon catheter 710 during insertion (positioning) of catheter assembly 700 to a region of interest within a blood vessel. Once catheter assembly 700 is positioned, sheath 705 may be retracted to expose balloon portion 715.

One way to locate balloon portion 715 of balloon catheter 710 at a region of interest is through MR tracking. Thus, in one embodiment, passive markers 750 may be positioned on catheter assembly 700. Referring to FIG. 6A, passive markers 750 are located, in this one example, on cannula 745 at a portion of cannula 745 corresponding with balloon portion 715 of balloon catheter 710. Passive markers 750 include materials that are detectable through MR imaging of the relevant vasculature. Such materials include metals such as titanium, tantalum, copper, aluminum, gold, nitinol, platinum, brass, silver, or polymeric materials with powdered metals extruded therewith. Representatively, gold materials with low magnetic susceptibility that will not be attracted to the scanner strong magnetic field may be extruded with polymeric materials. In one embodiment, passive markers 750 are flat wires of tantalum having a dimension on the order of 0.005 inches by 0.002 inches. Passive markers 750 may be used to locate balloon portion 715 at a region of interest.

As noted above, catheter assembly 700 includes balloon catheter 710 having balloon portion 715 that is a multi-lobed or fluted balloon portion. FIG. 6B illustrates a cross-sectional view through line A-A' of FIG. 6A. FIG. 6B shows balloon portion 715 having three lobes (lobe 720A, 720B, and 720C). In one embodiment, lobes 720A, 720B, and 720C are independently inflatable lobes. In one embodiment, separate lumens 725A, 725B, and 725C, for each of lobes 720A, 720B, and 720C, respectively, extend to manifold 760 (see FIG. 6A) at a proximal end of catheter assembly 700. Referring to FIG. 6A, catheter assembly 700 includes inflation port 765 to introduce a suitable fluid to inflate lobes 720A, 720B, and 720C and manifold 760 to direct inflation fluid into the appropriate lumen and lobe. Individual valves 762A, 762B, and 762C on manifold 760 may be used to control the inflation of respective lobes.

FIG. 6B shows balloon portion 715 in an inflated state with lobes 720A, 720B, and 720C inflated to a similar size. Cannula 745 extends through balloon portion 715 (through lumen 740). Conductive element 730 is disposed in cannula 745 as an imaging element (e.g., an MR antenna or coil). Lobe portions 720A, 720B, and 720C may be used to align conductive element 730 at an axial position within a blood vessel. For example, in one embodiment, it may be desirable to have conductive element 730 axially centered within a blood vessel. In such case, each of lobes 720A, 720B, and 720C will be inflated to a diameter to achieve such centering. It is appreciated that the amount of inflation of individual lobes may not be equivalent as the composition of a blood vessel wall at a region of interest may vary significantly, with, for example, lipid or fibrous material including, thin-capped fibroatheromas (TCFAs). Thus, the ability to independently inflate lobes of a balloon portion allows centering of an imaging device in a non-concentric region of interest.

In addition to providing a technique for centering an imaging device, such as an MR imaging device, the multi-lobed or fluted balloon portion 715 provides regions between lobe portions to allow fluid (e.g., blood) perfusion through or by balloon portion 715. In this manner, balloon portion 715, in an inflated or expanded state, will not block blood flow through the blood vessel during an imaging procedure.

FIG. 6C shows a cross-sectional view of catheter assembly 700 through line B-B'. In this embodiment, balloon catheter 710 is shown having lumens 725A, 725B, and 725C corresponding to lobes 720A, 720B, and 720C, respectively. Lumens 725A, 725B, and 725C transport fluid to the respective lobes. It is appreciated, that balloon catheter 710 may be a single body having lumens 725A, 725B, and 725C therethrough or lumens 725A, 725B, and 725C, may represent lumens of individual cannulas collected in the lumen of a larger cannula (e.g., balloon catheter 710). FIG. 6C also shows balloon catheter 710 having lumen 740 through which cannula 745 is placed. Cannula 745 has a lumen of a size suitable to accommodate conductive element 730 such as an MR imaging antenna or coil. In addition to conductive element 730, cannula 745 may include circuit elements of, for example, MR circuitry disposed therein. Alternatively, conductive element 730 may be connected to MR circuitry, such as described above, external to catheter assembly 700. FIG. 6A shows conductive element 730 extending through imaging port 755 of catheter assembly 700.

Figure 6D:
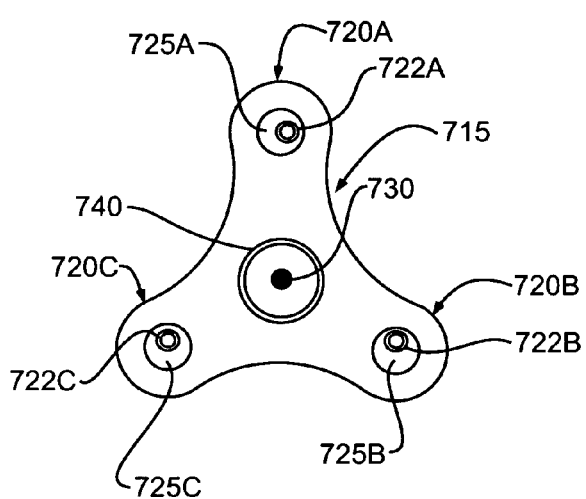
FIG. 6D shows a cross-sectional view of another embodiment of the catheter assembly of FIG. 6A through line A-A'.
Figure 6E:
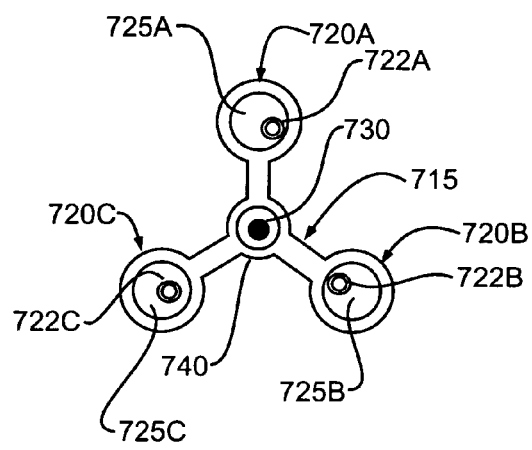
FIG. 6E shows a cross-sectional view of another embodiment of the catheter assembly of FIG. 6A through line A-A'.

Referring again to FIG. 6B, inflatable lobes 720A, 720B, and 720C are shown each having a generally equal diameter. Representatively, each lobe may have a diameter in a range of approximately 0.5 mm (non-inflated) to 5 mm (fully inflated). It is appreciated that one or more lobes may have different diameters (e.g., asymmetrical, lopsided) that may be formed by extrusion techniques. FIG. 6D and FIG. 6E show various other embodiments for balloon portion 715 of balloon catheter 710, representatively through line A-A' of FIG. 6A.

Figure 7A:
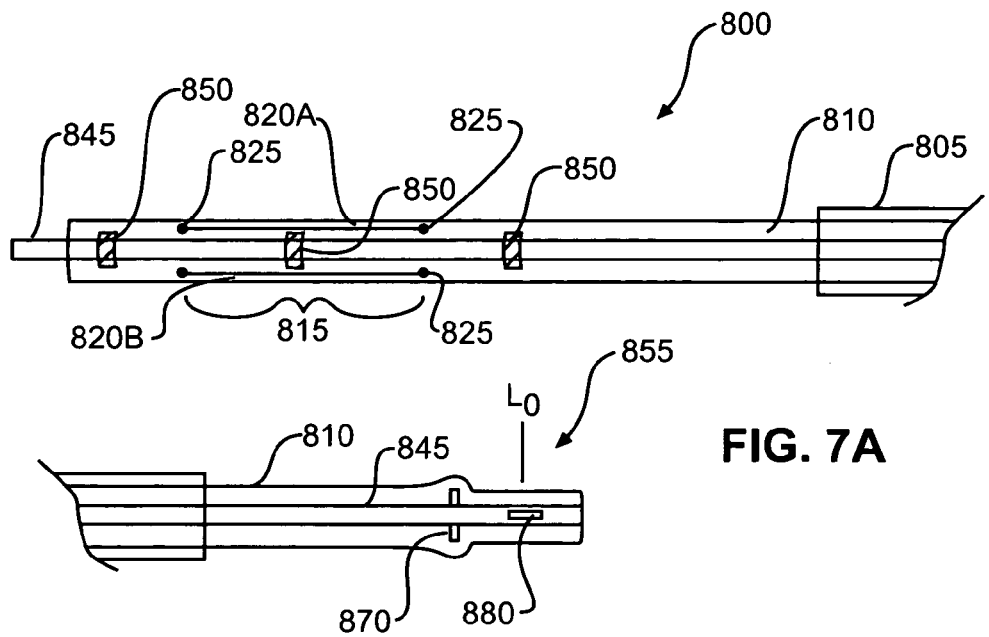
FIG. 7A illustrates an embodiment of a catheter assembly including a coaxial shaft and an antenna aligned with the shaft.
Figure 7B:
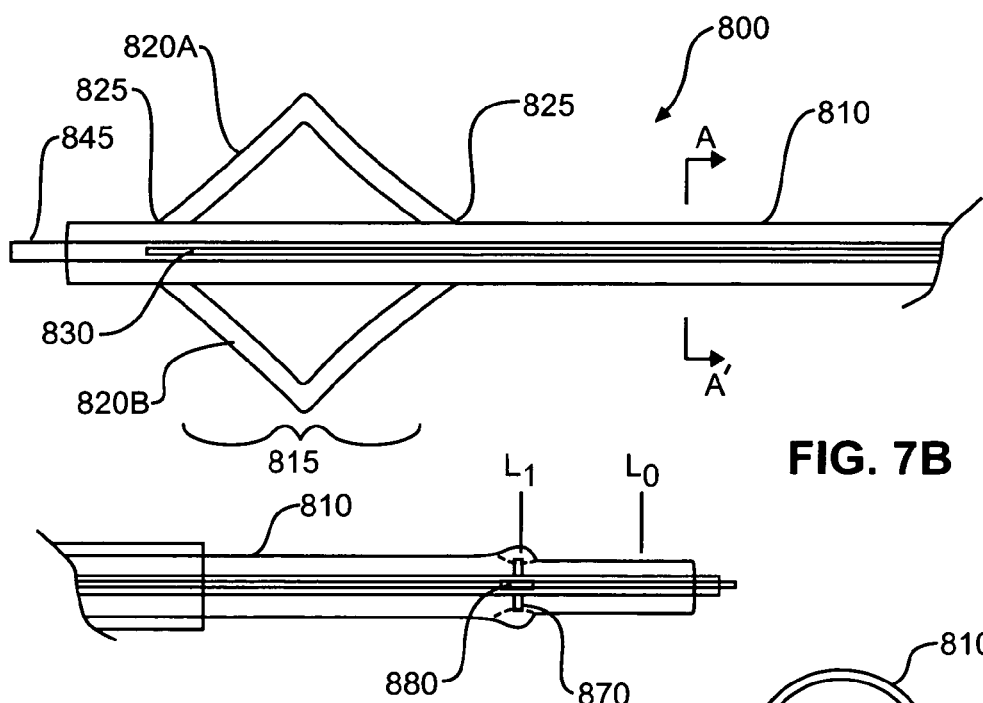
FIG. 7B shows the catheter assembly of FIG. 7A with a cage portion of one cannula in an expanded configuration.
Figure 7C:
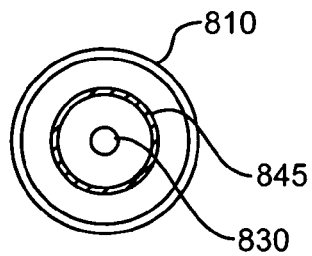
FIG. 7C shows a cross-sectional view of the catheter assembly of FIG. 7A through line A-A' of FIG. 7B.

FIGS. 7A-7C illustrate another embodiment of a catheter assembly. Catheter assembly 800 includes, in this embodiment, a coaxial shaft including outer cannula 810 and inner cannula 845 positioned within outer cannula 810. Outer cannula 810 and inner cannula 845 are each made of MR compatible materials such as PEEK or braided nylon. Inner cannula 845 has, for example, a lumen of a diameter sufficient to be inserted over a guidewire and advanced to a region of interest within a blood vessel. Inner cannula 845 is also used, in this embodiment, for an MR imaging antenna with any guidewire either serving as an MR imaging antenna or being removed to allow advancement of an MR imaging antenna through a lumen of inner cannula 845. FIG. 7A also shows passive markers 850 connected to inner cannula 845. Passive markers are, for example, MR detectable markers that may provide identification of a location of a distal portion of catheter assembly 800 within a blood vessel of a patient. In this embodiment, passive markers 850 are, for example, flat wire bands of, for example, titanium, tantalum, etc.

Outer cannula member 810 includes an opening or cage portion at a distal portion to expand a diameter of outer cannula member 810. In one embodiment, cage portion 815 of outer cannula member 810 includes a number of fillets, illustrated as fillet 820A and 820B. In this embodiment, fillets 820A and 820B can expand outwardly in response to a longitudinally-applied force, such as a push (collapse) or pull (expand) force directed on outer cannula 810. In one embodiment, fillets 820A and 820B are intended to bend and expand cage portion 815 radially in response to a longitudinal force directed in a direction from proximal to distal (i.e., a collapse or pushing on outer cannula 810). In order to expand radially, cage portion 815 includes a number of stress points 825 that may be holes, grooves, or similar deflection (e.g., weak) points in outer cannula 810. Stress points 825 designate the location where outer cannula 810 will give and where fillets will bend. Thus, a size of cage portion 815, including a cross-sectional length or diameter, is controlled by longitudinal lengths of fillets 820A and 820B and the size (e.g., lateral dimension or diameter). A sequence or configuration of cage portion 815 in an expanded position may be controlled by a stiffness variation of the pattern of stress points 825. In the embodiment shown in FIG. 7A, stress points 825 are shown at ends of each fillet. The number and location of stress points 825 may be varied to control the stiffness variation and configuration of cage portion 815. In one embodiment, a number of fillets are located at approximately a similar longitudinal position on outer cannula 810 and spaced radially around outer cannula 810. In another embodiment, one or more fillets may be located at different longitudinal positions on outer cannula 810 (e.g., different longitudinal and radial positions).

FIG. 7B shows catheter assembly 800 wherein cage portion 815 is in an expanded configuration. One way to expand cage portion 815 as shown is by a force applied in a longitudinal direction at proximal end of outer cannula 810 toward the distal end of the cannula. Referring to FIGS. 7A and 7B together, a force on outer cannula 810 by for example pushing a proximal end of outer cannula 810 toward its distal end and moving lever 870 from a first position, $L_0$, to a second position, $L_1$, translates into the expansion of cage portion 815 by bending fillets 820A and 820B at stress points 825. Lever 870 may be, for example, a protuberance or protuberances on inner cannula 845. To maintain the position of cage portion 815 in an open or expanded position, lever 870 may be locked through lock 880 which, in one example, is an opening in outer cannula 810 that can accommodate a portion of lever 870.

FIG. 7B shows catheter assembly 800 having cage portion 815 in an expanded configuration with the expansion shown as the projection of fillet 820A and fillet 820B. It is appreciated that there may be a number of possible fillets, such as from one to four or more fillets (e.g., disposed radially around a longitudinal position of outer cannula 810). In an expanded position, the fillets tend to maintain inner cannula 845 in a desired position within a blood vessel, such as centered in a blood vessel, at a region of interest. Conductive element 830 is disposed within a lumen of inner cannula 845.

FIG. 7C shows a cross-sectional view of catheter assembly 800 through lines A-A'. FIG. 7C illustrates conductive element 830 disposed within a lumen of inner cannula 845. Inner cannula 845 is shown within a lumen of outer cannula 810. Conductive element 830 may extend from a proximal end of catheter assembly 800 to be coupled to MR circuitry. Alternatively, certain MR circuitry may be positioned within inner cannula 845.

In addition to aligning (e.g., centering) a device such as conductive element 830 in a blood vessel, catheter assembly 800 also provides fluid (e.g., blood) perfusion about the assembly. In other words, the fillets are selected to be of a sufficient dimension and number to maintain conductive element 830 at a desired position (e.g., centered) within a blood vessel and to allow gaps or space between fillets for blood perfusion. As described above, fillet 820A and 820B and other fillets may be cuts or slits in outer cannula member 845 or may constitute tubular structures formed, for example, by extruding a multiple cannula cage portion 815 and connecting cage portion 815 to outer cannula 810.

FIGS. 8A-8D illustrate another embodiment of a catheter assembly. Catheter assembly 900 includes balloon catheter 910 including balloon portion 915 connected at a distal portion of balloon catheter 910. Balloon portion 915 may be a conventional balloon configuration utilized in a percutaneous angioplasty procedure. In one embodiment, balloon portion 915 is an MR compatible material such as PEBAX. Balloon catheter 910 is also an MR compatible material such as PEEK or braided nylon. Balloon portion 915 may be bonded to balloon catheter 910. In the embodiment shown in FIG. 8A, protuberances or stripes 920A and 920B are each connected longitudinally to the working length of balloon portion 915. Protuberances 920A and 920B have a thickness, t, that, in one sense, increases a diameter of balloon portion 915. It is appreciated that there may be a number of protuberances longitudinally disposed about a working length of balloon portion 915. Protuberances 920A and 920B may have a variety of forms including solid forms or hollow (e.g., tubular) forms that are connected, such as by bonding, to a working length of balloon portion 915. In one embodiment, protuberances 920A and 920B are made of a material that is MR compatible, including, for example, PEEK or braided nylon.

FIG. 8A also shows cannula 945 disposed through a lumen of balloon catheter 910 including through balloon portion 915. Cannula 945 is an MR compatible material such as PEEK or braided nylon. Cannula 945 may have a lumen suitable for accommodating a guidewire so that catheter assembly 900 may be introduced to a region of interest within a blood vessel over a guidewire. In one embodiment, a distal portion of cannula 945 may have a number of passive markers thereon that may be used for passive identification through, for example, MR imaging to locate catheter assembly 900 at a region of interest. In one embodiment, passive markers 950 are flat wire markers of, for example, titanium, tantalum, etc., each having a dimension on the order of 0.005 inches by 0.002 inches.

Catheter assembly 900 may optionally include sheath 905 on/over balloon catheter 910. Once catheter assembly 900 is positioned at a region of interest within a blood vessel, sheath 905 may be retracted to expose balloon portion 915. A guidewire used in such positioning may be removed leaving cannula 945 free and available for an imaging device. Representatively, an MR imaging coil or antenna may be inserted at entry port 955 at a proximal end of balloon catheter 910 through a lumen of cannula 945.

FIG. 8B shows catheter assembly 900 having balloon portion 915 in an inflated state. Balloon portion 915 may be inflated through inflation port 965. Representatively, balloon portion 915 is filled with a suitable liquid through entry port 965 until a diameter of a working part of balloon portion 915 approximates the inner diameter of a blood vessel at the region of interest. The inflation of balloon portion 915 locates protuberances 920A between a blood vessel wall and a working length of balloon portion 915 at a region of interest. In one embodiment, protuberances 920A and 920B (and any other protuberances) contact the interior wall of the blood vessel.

In the embodiment shown in FIG. 8B, protuberances 920A and 920B have a longitudinal dimension equivalent to a working length of balloon portion 915. In this embodiment, ends of protuberances 920A and 920B are tapered so as to approximate the angle of sidewalls of balloon portion 915. FIG. 8B shows protuberance 920A having a proximal end that is tapered at an angle, $\alpha$, to approximate the taper of the proximal sidewall of balloon portion 915.

Figure 8C:
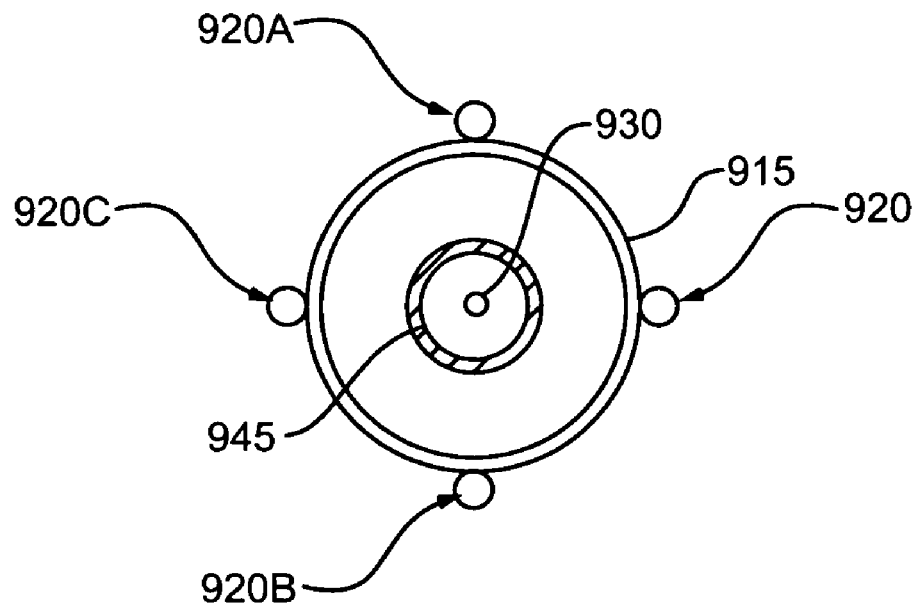
FIG. 8C shows a cross-sectional view of the catheter assembly of FIG. 8A through line A-A' of FIG. 8B.

Protuberances 920A and 920B (and any other protuberances) are longitudinally spaced to allow spaces or gaps between protuberances. The spaces or gaps permit fluid (e.g., blood) perfusion through the blood vessel during a procedure, such as an imaging procedure. FIG. 8C shows a cross-sectional view through line A-A' of FIG. 8B. FIG. 8C shows protuberances 920A, 920B, 920C, 920D spaced about balloon portion 915. The spaces between adjacent protuberances allow for blood perfusion. In a further embodiment, one or more protuberances 920A, 920B, and 920C are hollow or tubular structures. The hollow or tubular structures allow additional perfusion during a procedure, such as an imaging procedure.

Figure 8D:
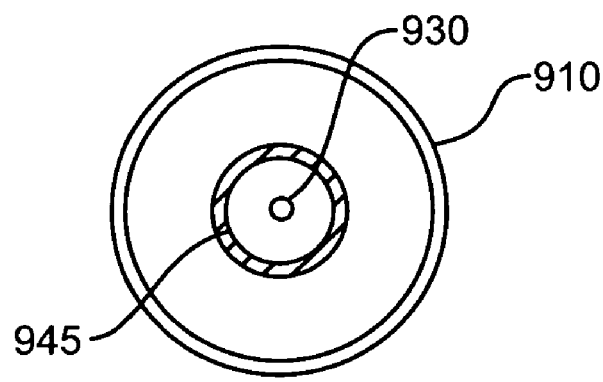
FIG. 8D shows a cross-sectional view of the catheter assembly of FIG. 8A of through line B-B'.

Referring again to FIG. 8B, conductive element 930 is shown disposed in a lumen of cannula 945. A distal end of conductive element 930 is positioned in or through balloon portion 915. A proximal end of conductive element may extend through port 955 at a proximal end of balloon catheter 910 (see FIG. 8A) to imaging circuitry such as MR imaging circuitry. Alternatively, certain MR imaging circuitry may be positioned within cannula 945 to improve a reception of a signal. FIG. 8D shows a cross-sectional side view through line B-B'. FIG. 8D shows conductive element 930 disposed in a lumen of cannula 945. Cannula 945 itself is disposed in a lumen of balloon catheter 910.

FIGS. 9A-9G show other embodiments of a catheter assembly. Catheter assembly 1000 of FIG. 9A includes a coaxially configured catheter shaft including inner cannula 1045 disposed in a lumen of outer cannula 1010. Outer cannula 1010 is shown disposed within sheath 1005 that may optionally be used, for example, during location (positioning) of catheter at a region of interest. Inner cannula 1045 has a lumen suitable, in one embodiment, for insertion of catheter assembly 1000 over a guidewire. In such manner, catheter assembly 1000 may be positioned at a region of interest within a blood vessel of a patient over such guidewire. Catheter assembly 1000 may include one or more passive markers, such as titanium or tantalum flat wire bands (e.g., 0.005 inches by 0.002 inches) on inner cannula 1045. Passive markers 1050 may be used to locate a distal portion of catheter assembly 1000 at a region of interest.

Figure 9A:
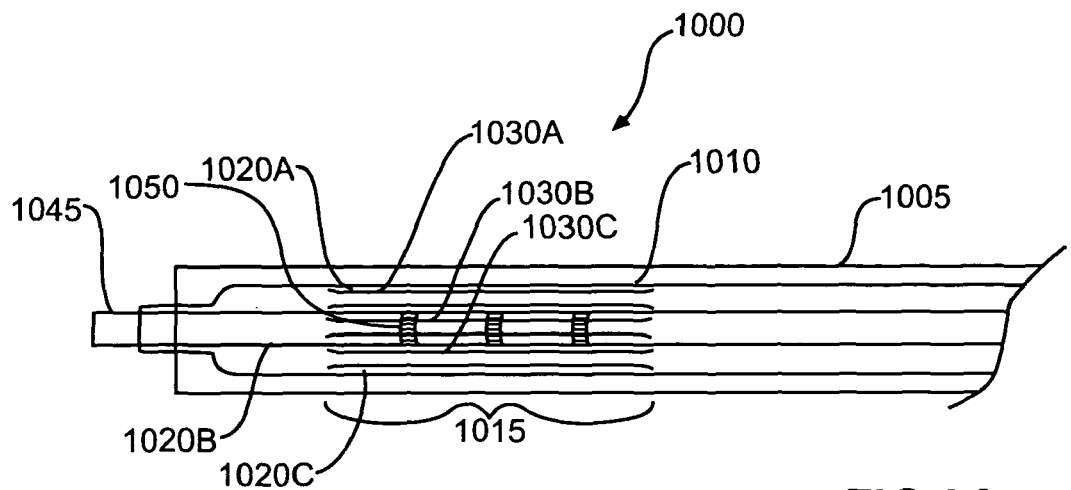
FIG. 9A illustrates an embodiment of a catheter assembly including a coaxial shaft of two cannulas with a portion of one cannula including a radially expandable cage portion of radially expandable fillets.

Outer cannula 1010 of catheter assembly 1000 includes cage portion 1015 of a number of fillets, illustrated in FIG. 9A as 1020A, 1020B, and 1020C. The fillets are defined by longitudinal cuts, slits, or divisions, in outer cannula 1010. The pattern and material selected for the number of fillets is selected, in one embodiment, to permit radial expansion of a cross-sectional diameter of outer cannula 1010 to, for example, a size similar to the interior diameter of a blood vessel at a region of interest. In FIG. 9A, the individual cuts, slits, or divisions between fillets are each of approximately similar length. A variation in the lengths is also contemplated. FIG. 9A shows fillets 1020A, 1020B, and 1020C approximately axially aligned defining a compacted or closed state for outer cannula 1010. The opening (expansion) and closing (compaction) of the number of fillets (including fillet 1020A, fillet 1020B, and fillet 1020C) is controlled by a longitudinally directed force applied at a proximal end of catheter assembly 1000. FIG. 9A shows lever 1070 within a lumen of outer cannula 1010. In this view, lever 1070 is at a position, $L_0$, and outer cannula 1010 is in a closed (collapsed) configuration. Applying a longitudinal force to a proximal end of outer cannula 1010 in a distal direction will cause the number of fillets to open or radially expand in response to the longitudinal force.

In the embodiment shown in FIG. 9A, a number of conductive elements are connected to respective ones of the number of fillets. FIG. 9A shows conductive element 1030A connected to fillet 1020A; conductive element 1030B connected to fillet 1020B; and conductive element 1030C connected to fillet 1020C. Conductive elements 1030A, 1030B, and 1030C are, in one embodiment, imaging antennas or coils, such as MR imaging antennas or coils. Thus, a proximal end of each of conductive elements 1030A, 1030B, and 1030C are connected to MR imaging circuitry, such as through entry port 1055.

Figure 9B:
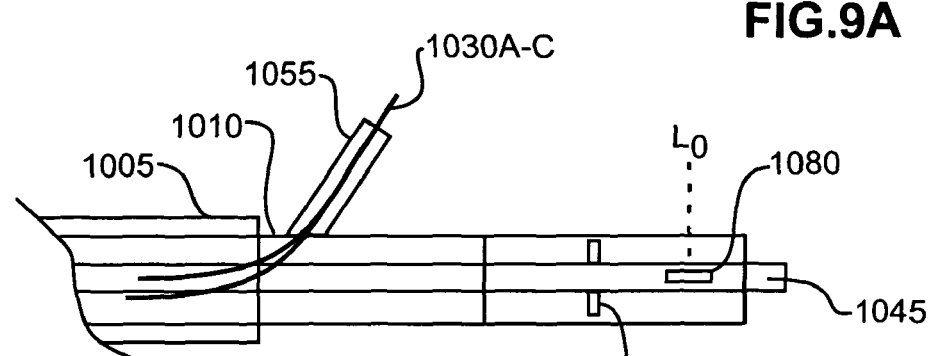
FIG. 9B shows the catheter assembly of FIG. 9A having a cage portion in an open or radially-expanded configuration.
Figure 9B:
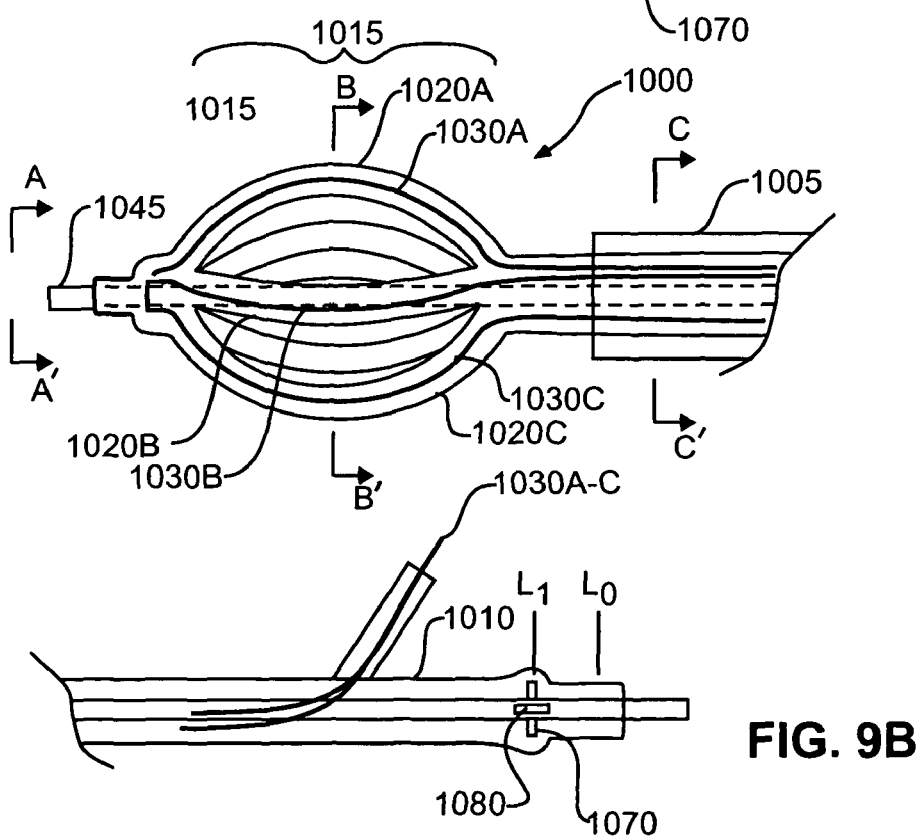

FIG. 9B shows catheter assembly 1000 having cage portion 1015 of outer cannula 1010 in an open or radially-expanded configuration. To open or expand the number of fillets (including fillets 1020A, 1020B, and 1020C), a longitudinal force is applied in a distal direction at a proximal end of outer cannula 1010. FIG. 9B shows lever 1070 at a position, $L_1$, that is distal to position, $L_0$, to indicate the force applied to outer cannula 1010. At a desired position, lever 1070 may be locked through lock 1080 which may be, for example, an opening or other locking structure through outer cannula 1010.

FIG. 9B shows cage portion 1015 having a generally spherical configuration with fillets (including fillet 1020A, fillet 1020B, and fillet 1020C) each adopting a semi-circular configuration in response to a force applied at a proximal end of outer cannula 1010. In one embodiment, a diameter of the spherically-shaped cage portion 1015 is similar to an inner diameter of a blood vessel so that one or more fillets contact an interior wall of the blood vessel. As shown in FIG. 9B, as each fillet expands, the conductive element connected to respective ones of the fillets (e.g., conductive element 1030A, conductive element 1030B, conductive element 1030C) adopt a similar shape.

Figure 9C:
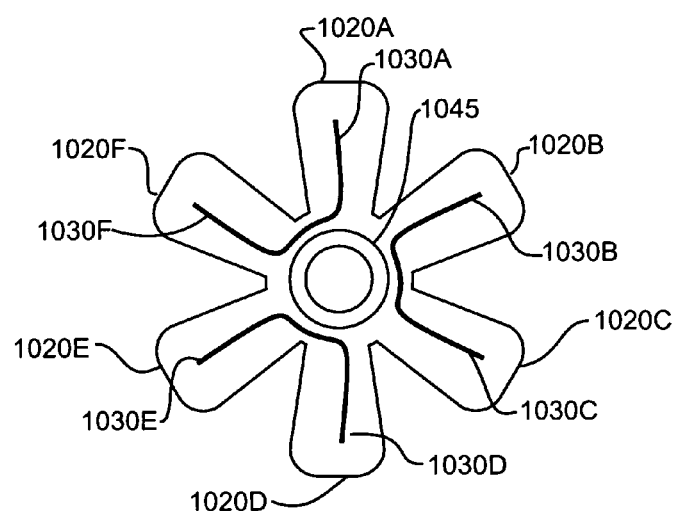
FIG. 9C shows a cross-sectional view of the catheter assembly FIG. 9A through line A-A' of FIG. 9B.

FIG. 9C shows catheter assembly 1000 through line A-A' of FIG. 9B, illustrating a distal end of catheter assembly 1000. From this view, a distal end of individual fillets 1020A, 1020B, 1020C, 1020D, 1020E, and 1020F are visible and shown having a circular profile. Also illustrated are conductive element 1030A (connected to fillet 1020A), conductive element 1030B (connected to fillet 1020B), conductive element 1030C (connected to fillet 1020C), conductive element 1030D (connected to fillet 1020D), conductive element 1030E (connected to fillet 1020E), and conductive element 1030F (connected to fillet 1020F). In this embodiment, pairs of conductive elements are connected together adopting a dipole antenna arrangement. Thus, conductive element 1030A is connected to conductive element 1030F; conductive element 1030B is connected to conductive element 1030C; and conductive element 1030D is connected to conductive element 1030E.

FIG. 9C also illustrates that, in an open (expanded) configuration, outer cannula 1010, including cage portion 1015, allows for fluid (e.g. blood) perfusion through the device. Thus, adjacent fillets are spaced from one another to allow perfusion between the fillets during a procedure, such as a imaging procedure.

Figure 9D:
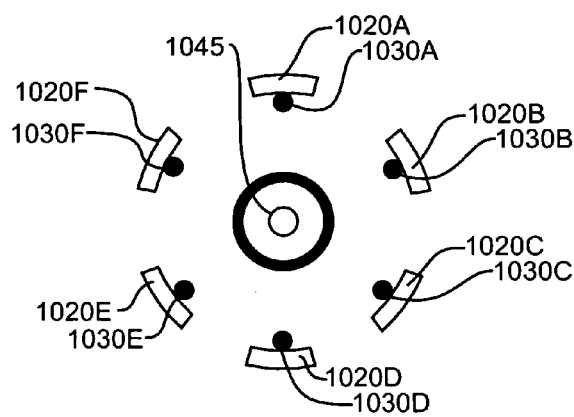
FIG. 9D shows a cross-sectional view of the catheter assembly of FIG. 9A through line B-B' of FIG. 9B.

FIG. 9D shows a cross-sectional view through line B-B' of catheter assembly 1000. Among other things, FIG. 9D shows individual fillets (fillet 1020A, fillet 1020B, 1020C, fillet 1020D, fillet 1020E, and fillet 1020F) spaced apart from one another and adopting a generally circular configuration. As illustrated, the fillets are sectioned or sliced components of a portion of outer cannula 1010. Connected to an interior side of each fillet, in this embodiment, is a conductive element (e.g., conductive element 1030A, conductive element 1030B, conductive element 1030C, conductive element 1030D, conductive element 1030E, and conductive element 1030F). In one embodiment, the individual conductive elements are a metallic material that is bonded to a polymeric material of the individual fillets. Thus, as the configuration of an individual fillet is modified, the configuration (shape) of the conductive element is similarly modified. A suitable conductive (e.g., metallic) material may have an elastic property to accommodate expansion and contraction of the fillets.

Figure 9E:
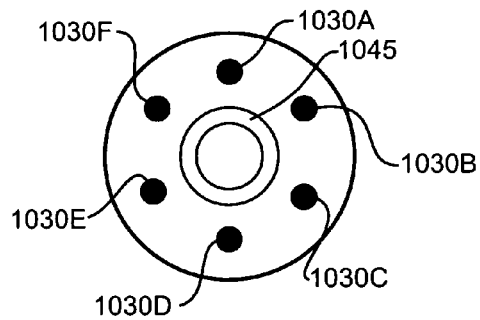
FIG. 9E shows a cross-sectional view of the catheter assembly of FIG. 9B through line C-C' of FIG. 9B.

FIG. 9E shows a cross-sectional view through line C-C' of FIG. 9B. FIG. 9E shows inner cannula 1045 disposed within a lumen of outer cannula 1010. Also disposed within a lumen of outer cannula 1010 are individual conductive elements (conductive element 1030A, conductive element 1030B, conductive element 1030C, conductive element 1030D, conductive element 1030E, and conductive element 1030F). The conductive elements are connected, in one embodiment, to imaging circuitry (e.g., MR imaging circuitry) external to catheter assembly 1000. In another embodiment, some circuitry may similarly be located in the lumen of outer cannula 1010.

In the above embodiment, the fillets of outer cannula 1010 were shown as slices or slits on a distal portion of outer cannula 1010. Individual conductive elements were connected to an underside (as viewed) portion of respective fillets. In one embodiment, the exposed fillets are insulated (e.g., an insulated wire). In another embodiment, a conductive element suitable for receiving MR signals may be disposed through a cannula within cage portion 1015, e.g., through a lumen of inner cannula 1045.

Figure 9F:
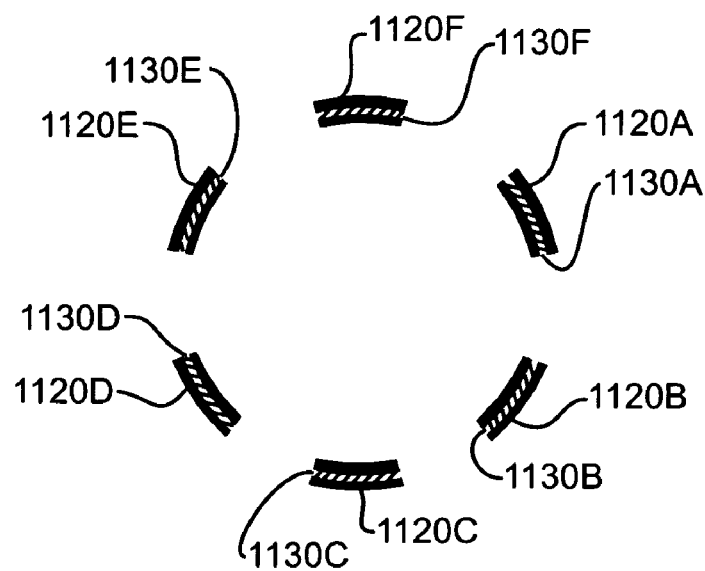
FIG. 9F shows an alternative embodiment of a cage portion of one cannula of the catheter assembly of FIG. 9A through line B-B' of FIG. 9B.

FIG. 9F shows an alternative embodiment of outer cannula 1010 (representatively through line B-B' of FIG. 9B). In this embodiment, the individual conductive elements (conductive element 1130A, conductive element 1130B, conductive element 1130C, conductive element 1130D, conductive element 1130E, and conductive element 1130F) are embedded in individual fillets (fillet 1120A, fillet 1120B, fillet 1120C, fillet 1120D, fillet 1120E, and fillet 1120F). The individual conductive elements may be embedded in individual fillets by constructing the fillets as two-part structures and in embedding through a deposit of conductive material between the fillet portions. By choosing a suitable polymer material for the fillet portions, the embedded conductive material may be electrically insulated. A suitable deposit technique for deposition of a metal material includes, but is not limited to, chemical vapor deposition (CVD). Alternatively, the individual fillets may be formed with conductive material therein through an extrusion process whereby a conductive element, such as a wire, is extruded through a die with outer cannula portion 1010.

Figure 9G:
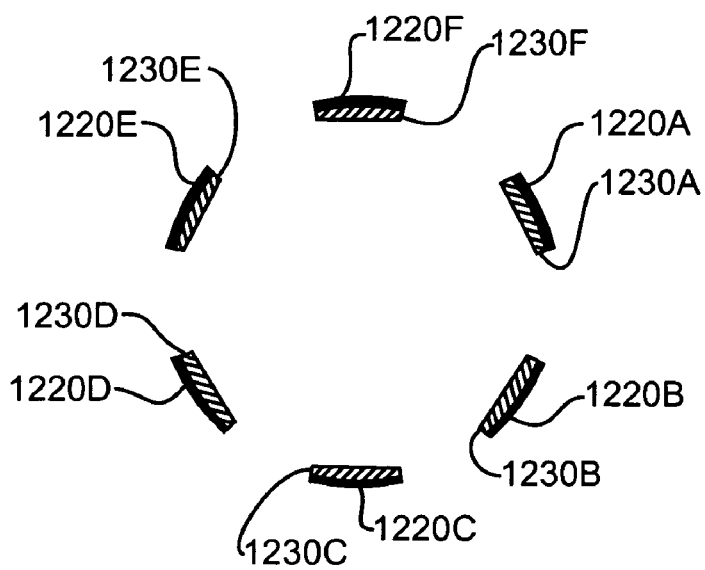
FIG. 9G shows an alternative embodiment of a cage portion of one cannula of the catheter assembly of FIG. 9A through line B-B' of FIG. 9B.
Figure 9H:
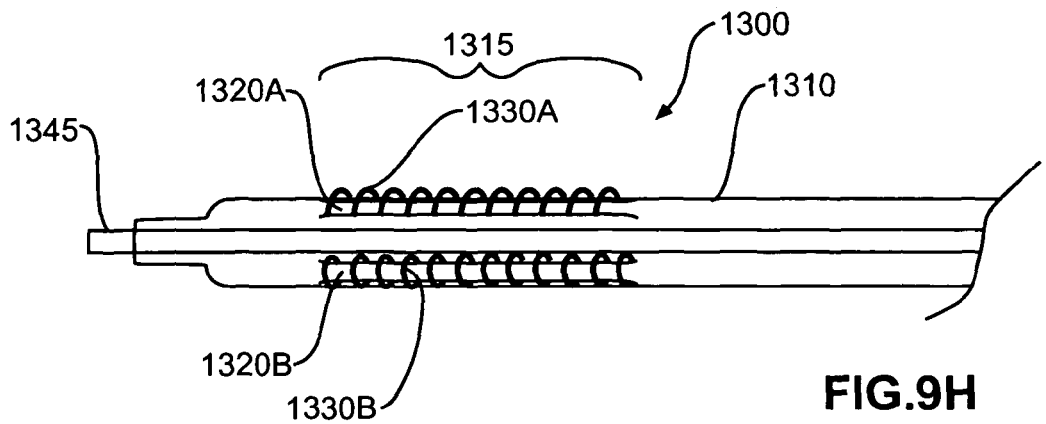
FIG. 9H illustrates a distal portion of an embodiment of a catheter assembly including a coaxial shaft of two cannulas with a portion of one cannula including a cage portion of radially-expandable fillet.
Figure 9I:
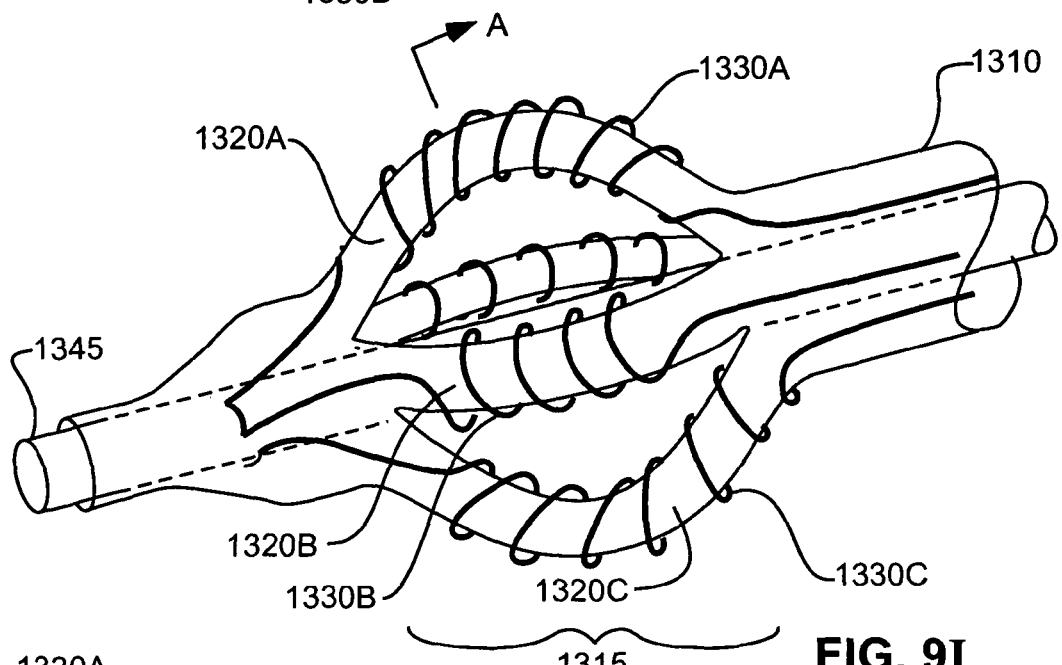
FIG. 9I shows the catheter assembly of FIG. 9H in a radially-expanded configuration.
Figure 9J:
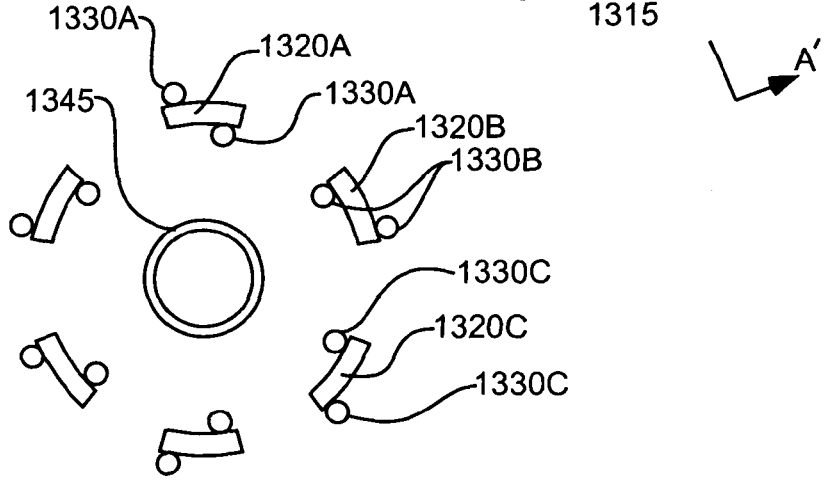
FIG. 9J shows a cross-sectional side view of the catheter assembly of FIG. 9H through line A-A' of FIG. 9I.

FIG. 9G shows another embodiment for connecting conductive elements to individual fillets. FIG. 9G representatively shows a cross-sectional view through line B-B' of FIG. 9B. In this embodiment, individual conductive elements (individual conductive element 1230A, individual conductive element 1230B, conductive element 1230C, conductive element 1230C, conductive element 1230D, conductive element 1230E, and conductive element F) are deposited on an underside (as viewed) of individual fillets (fillet 1220A, fillet 1220B, fillet 1220C, fillet 1220D, fillet 1220E, and fillet 1220F, respectively). In one embodiment, the individual conductive elements may be deposited on individual fillets through a deposition process of conductive material, such as chemical vapor deposition. In another embodiment, an insulating material may be deposited on the individual conductive elements. FIG. 9H, FIG. 9I and FIG. 9J show still further embodiments of a catheter assembly including a coaxially-configured catheter shaft. FIG. 9H and FIG. 9I show a distal end of catheter assembly 1300. In this embodiment, catheter assembly 1300 includes inner cannula 1345 disposed within a lumen of outer cannula 1310. Outer cannula 1310 and inner cannula 1345, in on embodiment, are MR compatible materials such as PEEK or braided nylon. Outer cannula 1310 includes cage portion 1315 including a number of fillet portions shown, in FIG. 9H, in a closed (collapsed) configuration to allow positioning at a region of interest within, for example, a blood vessel of a patient. Each individual fillet includes single or multiple loops of conductive material around the fillet body.

FIG. 9I shows cage portion 1315 of outer cannula 1310 in an open or radially-expanded configuration. Individual fillets (e.g., fillet 1320A, fillet 1320B, fillet 1320C) have conductive elements, such as a conductive wire (possibly an insulated wire) wrapped along their bodies. FIG. 9J shows cage portion 1315 through line A-A' of FIG. 9I. FIGS. 9I and 9J show fillet 1320A with conductive element 1330A wrapped concentrically along its length; fillet 1320B with conductive element 1330B wrapped along its length; and fillet 1320C with conductive element 1330C wrapped along its length. Representatively, each conductive element may have a diameter on the order of 0.001 inches to 0.01 inches. FIG. 9I also shows pairs of conductive elements connected to one another in a dipole antenna configuration. Specifically, conductive element 1330A is shown connected to conductive element 1330B. The individual conductive elements are connected, in one embodiment, at a proximal end of catheter assembly 1300 to imaging circuitry, such as MR imaging circuitry.

Figure 9K:
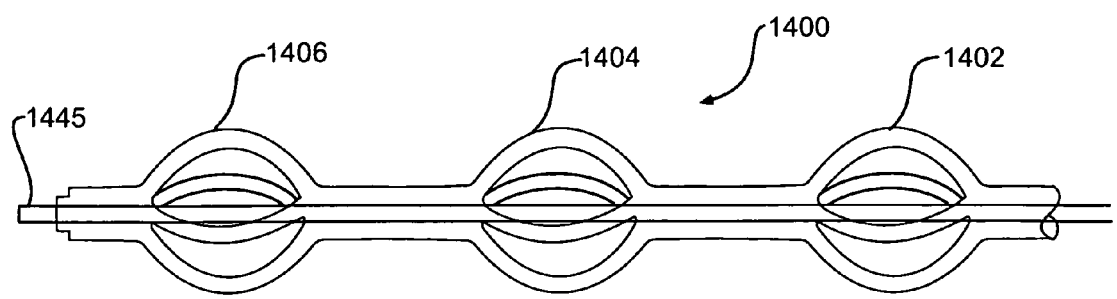
FIG. 9K illustrates a distal portion of an embodiment of a catheter assembly including a coaxial shaft of two cannulas with a portion of one cannula including a number of cage portions in series.

In the above embodiments (FIGS. 9A-9J), a catheter assembly including a single cage portion has been described. It is appreciated that such an assembly may have multiple cage portions along its length. FIG. 9K illustrates catheter assembly 1400 of a coaxial catheter configuration such as described above with respect to FIGS. 9A-9J and having cage portion 1402, cage portion 1404, and cage portion 1406 aligned in series along a distal portion of catheter assembly 1400. Each individual cage portion may be configured as described above with respect to FIGS. 9A-9J having expandable/collapsible fillet portions and conductive elements connected to individual fillet portions either as individual conductive elements or in pairs (e.g., dipole antennas) or groups. Alternatively, a conductive element may be disposed within a lumen of inner cannula 1445.

Figure 9L:
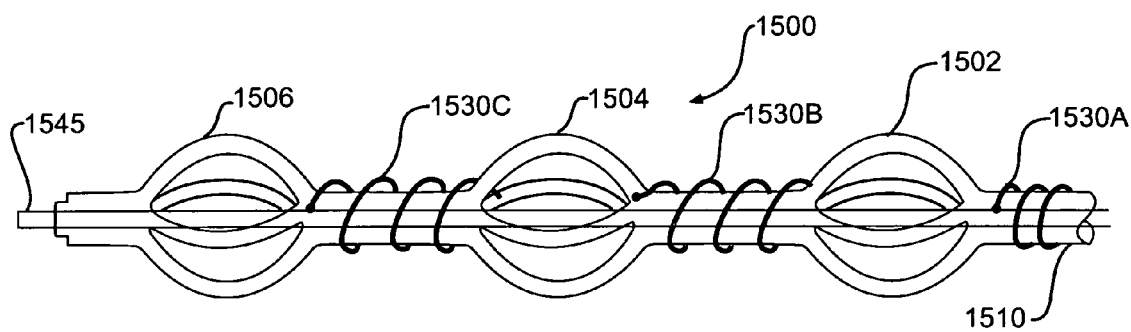
FIG. 9L illustrates a distal portion of an embodiment of a catheter assembly including a coaxial shaft of two cannulas with a portion of one cannula including a number of cage portions and an antenna wound between the cage portions.
Figure 9M:
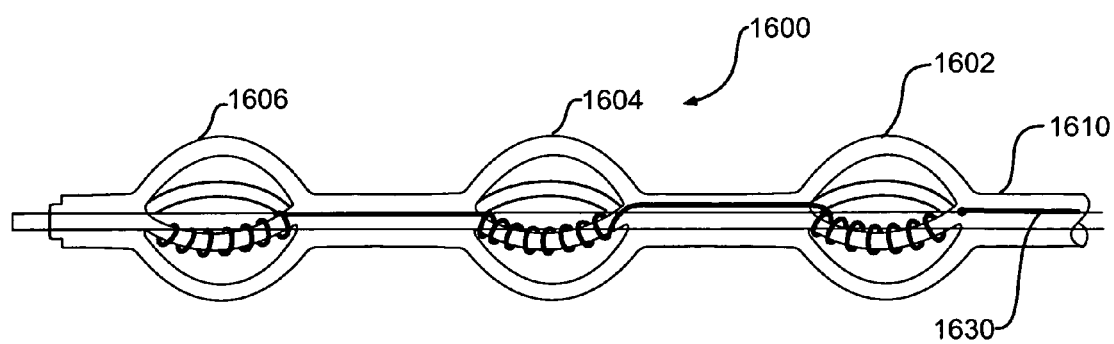
FIG. 9M shows distal portion of an embodiment of a catheter assembly including a coaxial shaft of two cannulas with a portion of one cannula including a number of cage portions and an antenna wound within the cage portions.

FIG. 9L illustrates another embodiment of a catheter assembly having a coaxial configuration. Catheter assembly 1500 includes inner cannula 1545 disposed within a lumen of outer cannula 1510. Outer cannula 1510 includes a number of cage portions, including, but not limited to, three cage portions such as cage portion 1502, 1504, and 1506. Cage portion 1502, cage portion 1504, and cage portion 1506 are expandable/collapsible cage portions such as described above in reference to FIGS. 9A-FIG. 9J and the accompanying text. Disposed between cage portions in FIG. 9L and wound/wrapped in a solenoid configuration around outer cannula 1510 are conductive elements (conductive element 1530A, conductive element 1530B, and conductive element 1530C). Conductive element 1530A, conductive element 1530B, and conductive element 1530C are, in one embodiment, individual (separate) conductive elements that serve as imaging devices (e.g., MR imaging antennas or coils) for imaging respective areas of, for example, a blood vessel or areas adjacent a blood vessel. It is appreciated that one or more conductive elements may extend between one or more cage portions in, for example, a dipole configuration. Conductive element 1530A, conductive element 1530B, and conductive element 1530C are, for example, wires that may or may not be insulated. In the embodiment shown, conductive element 1530A, conductive element 1530B, and conductive element 1530C are wound around outer cannula portion 1510 between cage portion 1502, cage portion 1504, and cage portion 1506, respectively, in a similar direction. It is appreciated that alternative directions may also be utilized. FIG. 9M shows another embodiment of a distal portion of a coaxially configured catheter assembly. Catheter assembly 1600 includes multiple cage portions (e.g., cage portion 1602, cage portion 1604, and cage portion 1606). Each cage portion has a number of fillets shown in an expanded configuration. Wound/wrapped in a solenoid configuration around one or more fillet portions, in this embodiment, is one or more conductive elements (illustrated as conductive element 1630). The conductive elements may be wound/wrapped around fillet portions in a similar or alternate direction or configuration (alternate configuration shown). In an embodiment having multiple conductive elements, pairs or groups of conductive elements may be connected together.

Figure 9N:
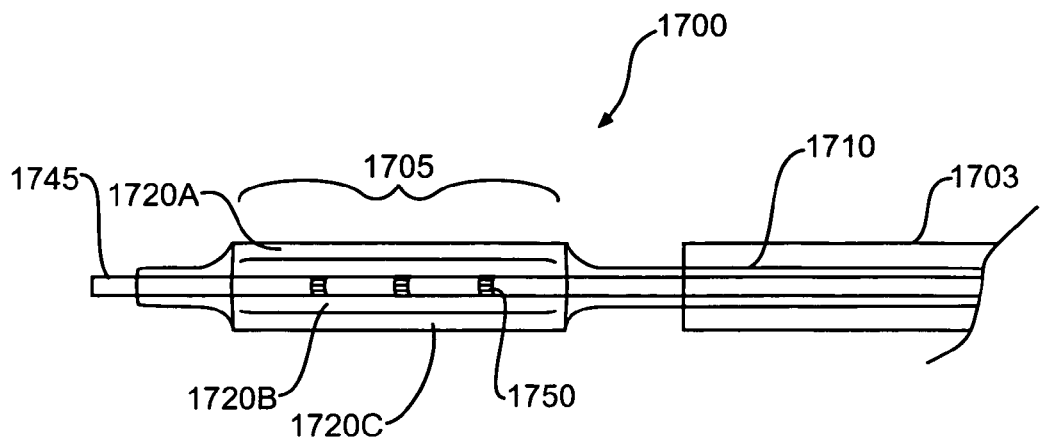
FIG. 9N illustrates a distal portion of an embodiment of a catheter assembly including a coaxial shaft of two cannulas with a portion of one cannula including a cage portion of cannula portions and an antenna disposed within the cannula portions.

FIGS. 9N-9R show another embodiment of a distal portion of a coaxial-configured catheter assembly. Catheter assembly 1700 includes, in this embodiment, inner cannula 1745 disposed through a lumen of outer cannula 1710. Outer cannula 1710 and inner cannula 1745 may be MR compatible materials such as PEEK or braided nylon. Inner cannula 1745 includes a lumen having dimensions suitable for a guidewire so that catheter assembly 1700 may be advanced over the guidewire to a region of interest. Catheter assembly 1700 may optionally include sheath 1703 over the entire portion of outer cannula 1710. Sheath 1703 may be removed (retracted) once catheter assembly 1700 is positioned at a region of interest. Referring to FIG. 9N, sheath 1703 is retracted proximally from a distal portion. To position catheter assembly 1700 at a region of interest, for example, within a blood vessel of a patient, catheter assembly 1700 may include a number of passive markers 1750 that are, for example, detectable on MR imaging. Passive markers include, but are not limited to, flat metal wires, such as titanium, tantalum, etc.

In this embodiment, outer cannula 1710 includes a multi-lumen shaft. At a distal portion, the multiple lumens may be separated/segmented into individual fillets defining cage portion 1705. Cage portion 1705 may be expanded/collapsed by a longitudinal force applied at a proximal end of catheter assembly 1700. One way to expand/collapse cage portion 1705 is described in reference to FIGS. 9A-9B and the accompanying text. FIG. 9N shows catheter assembly 1700 in a collapsed configuration having cage portion 1705 of axially-aligned fillets (e.g., fillet 1720A, fillet 1720B, and fillet 1720C). As part of the multi-lumen structure of outer cannula 1710, the respective lumens of the multi-lumen structure, including the multiple fillets, each include a conductive element that may be used, for example, for imaging applications such as MR imaging.

Figure 9O:
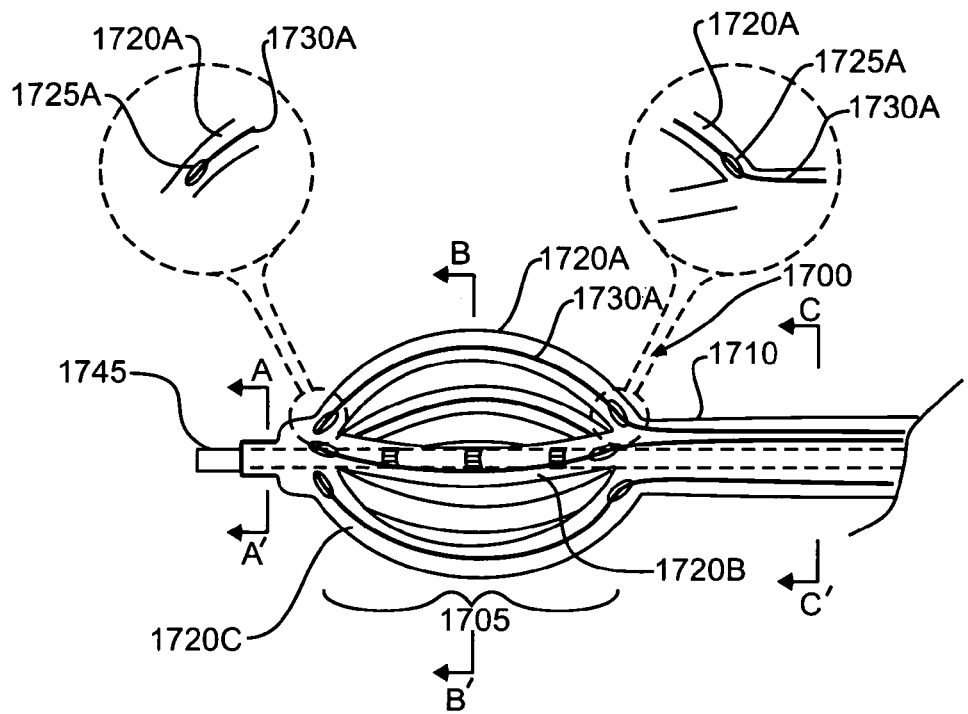
FIG. 9O shows the catheter assembly of FIG. 9N with the cage portion in a radially-expanded configuration.

FIG. 9O shows catheter assembly 1700 with cage portion 1705 in a radially-expanded configuration. Cage portion 1705, in this embodiment, includes multiple fillets each comprising a cannula structure. A multiple cannula structure may be formed, in one embodiment, by an extrusion technique. Representatively, FIG. 9O shows fillet 1720A of cage portion 1705. Fillet 1720A is a cannular structure having a lumen therethrough. Disposed within the lumen of cannula 1720A is conductive element 1730A. Fillet 1720A also includes openings 1725A and 1735A at a proximal and distal end of the fillet, respectively. Opening 1725A and opening 1735A provide, in one embodiment, stress points for the expansion/collapse of fillet 1720A. The other fillets that make up cage portion 1705 may be configured in a similar fashion.

Figure 9P:
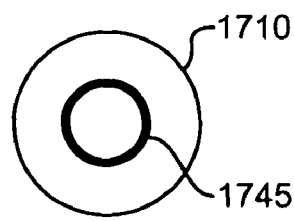
FIG. 9P shows a cross-sectional view of the catheter assembly of FIG. 9M through line A-A' of FIG. 9N.

FIG. 9P shows a cross-sectional view through line A-A'. FIG. 9P shows the coaxial configuration of inner cannula 1745 and outer cannula 1710. The multi-cannula structure of outer cannula 1710 may terminate at a distal end of catheter assembly 1700 as shown, through connecting (bonding) to a single lumen shaft (illustrated as a distal end of outer cannula 1710).

Figure 9Q:
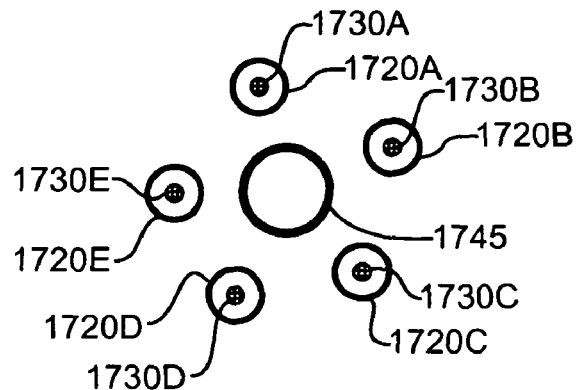
FIG. 9Q shows a cross-sectional view of the catheter assembly of FIG. 9N through line B-B' of FIG. 9O.

FIG. 9Q shows catheter assembly 1700 through line B-B'. In this view, the individual cannulas that describe fillets of cage portion 1705 are illustrated. Representatively, FIG. 9P shows fillet 1720A including conductive element 1730A coaxially-disposed therein; fillet 1720B including conductive element 1730B coaxially-disposed therein; fillet 1720C including conductive element 1730C coaxially-disposed therein; fillet 1720D including conductive element 1730D coaxially-disposed therein; and fillet 1720E including conductive element 1730E coaxially-disposed therein. FIG. 9Q also shows the fillets of cage portion 1705 spaced or separated from one another to allow fluid (e.g., blood) perfusion when cage portion 1705 is in a radially-expanded (opened) state (e.g., blood perfusion between adjacent fillets).

Figure 9R:
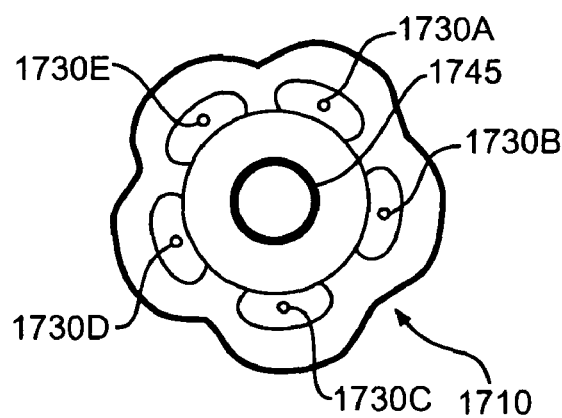
FIG. 9R shows a cross-sectional view of the catheter assembly of FIG. 9N through line C-C' of FIG. 9O.

FIG. 9R shows catheter assembly 1700 through line C-C'. From this view, the multi-lumen structure of outer cannula 1710 is illustrated. Representatively, outer cannula 1710 includes five lumens including conductive element 1730A, conductive element 1730B, conductive element 1730C, conductive element 1730D, and conductive element 1730E, respectively. Conductive element 1730A-1730E may be individual conductive elements or may be connected to one another. A conductive end of conductive element 1730A-1730E may extend beyond a proximal end of catheter assembly 1700 and be connected to imaging circuitry, such as MR imaging circuitry.

Figure 10A:
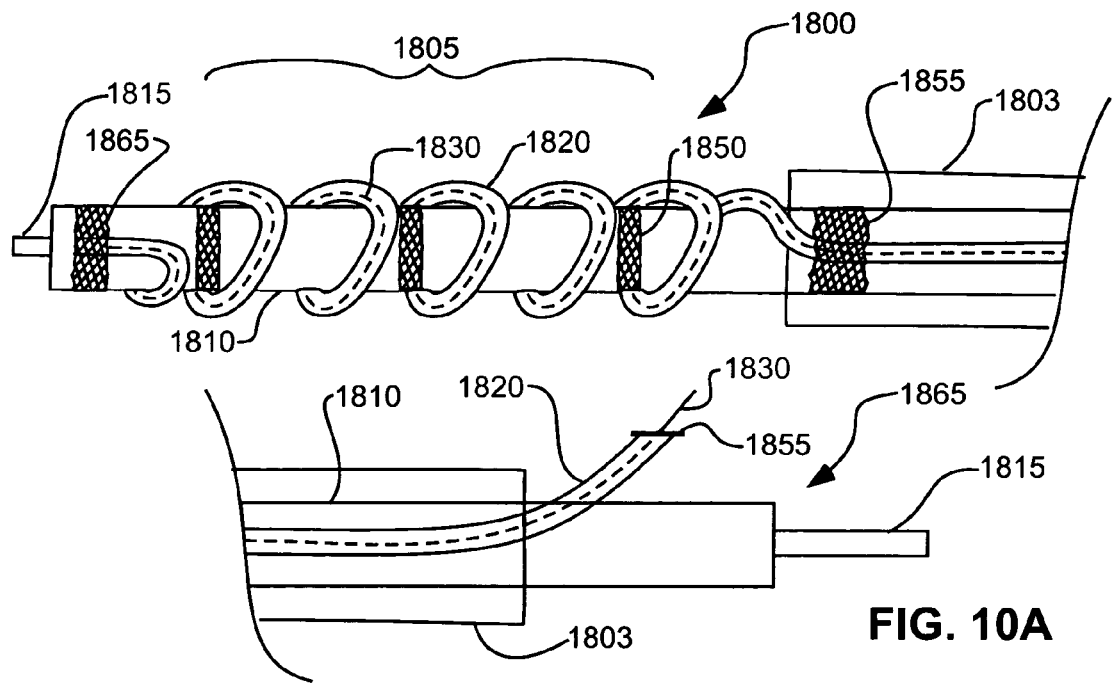
FIG. 10A illustrates an embodiment of a catheter assembly including a first cannula and a second cannula having a balloon portion wound around a portion of the first cannula.
Figure 10B:
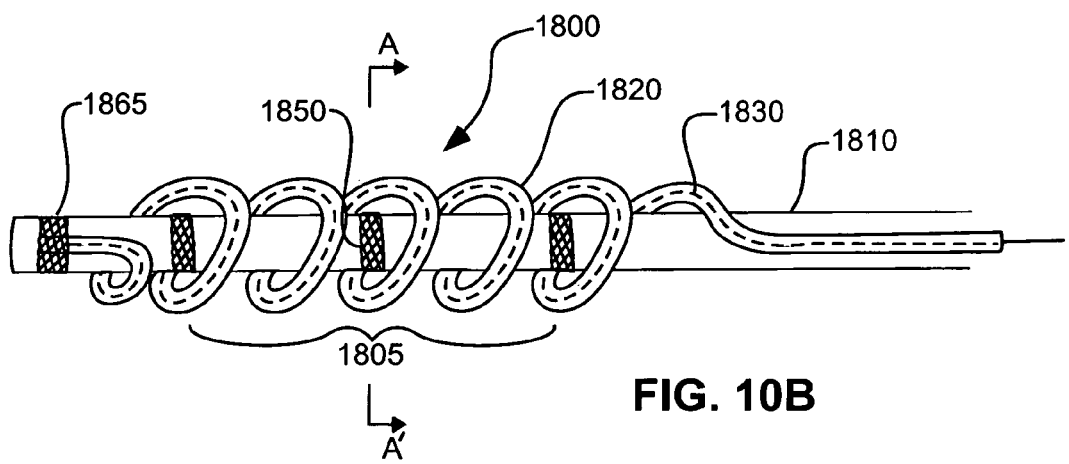
FIG. 10B shows a distal portion of the catheter assembly of FIG. 10A having the balloon portion in an inflated (expanded) state.
Figure 10C:
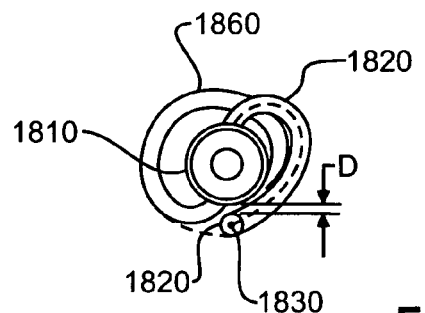
FIG. 10C shows a cross-sectional view of the catheter assembly of FIG. 10 through line A-A' of FIG. 10B.

FIGS. 10A-10C show another embodiment of a catheter assembly. Catheter assembly 1800 includes cannula 1810 that has a lumen of a sufficient size (diameter) to accommodate a guidewire, such as guidewire 1815. In this manner, catheter assembly 1800 may be advanced over guidewire 1815 to a region of interest. Cannula 1810 may be an MR compatible material such as PEEK or braided nylon. To locate cannula 1810 at a region of interest within a blood vessel of a patient, cannula 1810 may include a number of passive markers 1850, such as passive MR imaging markers. One type of passive marker includes a flat wire band of titanium, tantalum, etc. (e.g., a dimension of 0.005 inches by 0.002 inches)

In addition to cannula 1810, catheter assembly 1800 includes balloon catheter 1820 wrapped/wound around cannula 1810. Balloon catheter 1820 is an MR compatible material that may be radially-expanded such as PEBAX. Disposed within a lumen of balloon catheter 1820 is conductive element 1830. Conductive element 1830 is, for example, an imaging device, such as an MR imaging antenna or coil. Conductive element 1830 may or may not be insulated along its length within balloon catheter 1820. Representatively, conductive element 1830 is a wire or ribbon disposed within the lumen of balloon catheter 1820. Alternatively, that portion of conductive element 1830 disposed within balloon catheter 1820 may be a deposited conductive layer (e.g., CVD deposited metal material) on an interior wall of balloon catheter 1820. A further embodiment includes a conductor embedded in a wall of balloon catheter 1820. In still a further embodiment, conductive element 1830 may be located in cannula 1810 such as by substituting guidewire 1815 for conductive element 1830 once the catheter assembly is placed at a region of interest or utilizing a guidewire that may also serve as a conductive element for receiving MR signals.

As shown in FIG. 10A, balloon portion 1820 is wrapped around a distal portion of cannula 1810. Balloon catheter 1820, in one embodiment, is wrapped/wound around cannula 1810 only at a distal portion where catheter assembly 1800 is positioned at a region of interest. FIG. 10A shows balloon portion 1820 wrapped/wound around cannula 1810 in a region defining distal segment 1805 of cannula 1810. At a proximal end of distal segment 1805, balloon catheter 1820 is fastened to cannula 1810 by strap 1855. Strap 1855 is, for example, an MR compatible material such as nylon or nylon braid that wraps around cannula 1810 and holds balloon catheter 1820 adjacent to cannula 1810. At a distal end of segment 1805, strap 1865, similar to strap 1855, affixes balloon catheter 1820 to cannula 1810.

In one embodiment, with the exception of the wrapped/wound portion of balloon catheter 1820 at segment 1805, balloon portion 1820 extends adjacent to or linearly with cannula 1810. Catheter assembly 1800 may include catheter sheath 1803 having a dimension (e.g., lumen) of a sufficient size to encompass balloon catheter 1820 (in a deflated state) and cannula 1810. Catheter sheath 1803 may be retracted once catheter assembly 1800 is placed at a region of interest, retracted at least to expose segment 1805. A proximal end of balloon catheter 1820 includes inflation port 1855.

FIG. 10A shows conductive element 1830 extending from a proximal end of inflation port 1855. Conductive element 1830 may be connected to imaging circuitry, such as MR imaging circuitry. A proximal end of catheter assembly 1800 also shows entry port 1865 for advancing the assembly over a guidewire (e.g., guidewire 1815).

FIG. 10B shows catheter assembly 1800 having balloon catheter 1820 in an inflated (radially-expanded) state. In one embodiment, the inflation of balloon catheter 1820 separates balloon catheter 1820 from cannula 1810, at least within coil segment 1805. In another embodiment, balloon catheter 1820 may remain in contact with cannula 1810 in coil segment 1805 while in an expanded state.

FIG. 10C shows a cross-sectional view through line A-A'. In this view, balloon catheter 1820, in an inflated state, increases the diameter of catheter assembly 1800. In one embodiment, the inflation (radial expansion) of balloon catheter 1820 is such that balloon catheter 1820 is adjacent to or contacts an interior wall of a blood vessel (illustrated as reference numeral 1860). As shown, the coiled configuration of balloon portion 1820 will permit fluid (e.g., blood) perfusion while balloon portion 1820 is in an inflated (expanded) state. FIG. 10C also shows balloon catheter 1820 separated from cannula 1810 by a distance, D.

Figure 11A:
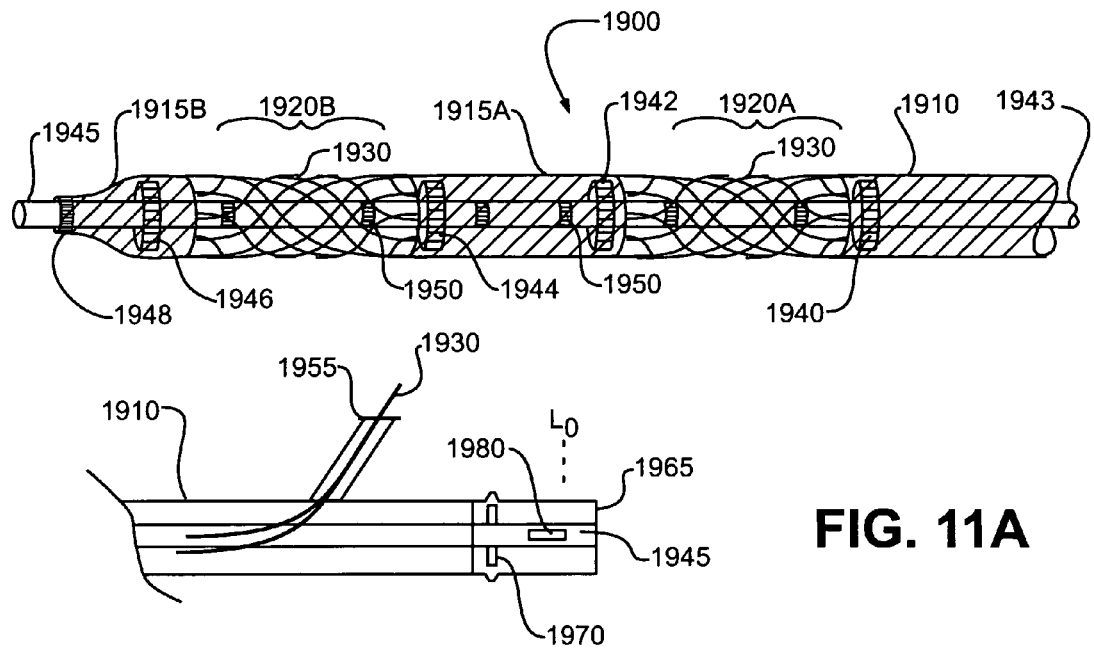
FIG. 11A illustrates an embodiment of a catheter assembly including a coaxial shaft of two cannulas with a distal portion of one cannula including a number of braided cage portions.
Figure 11B:
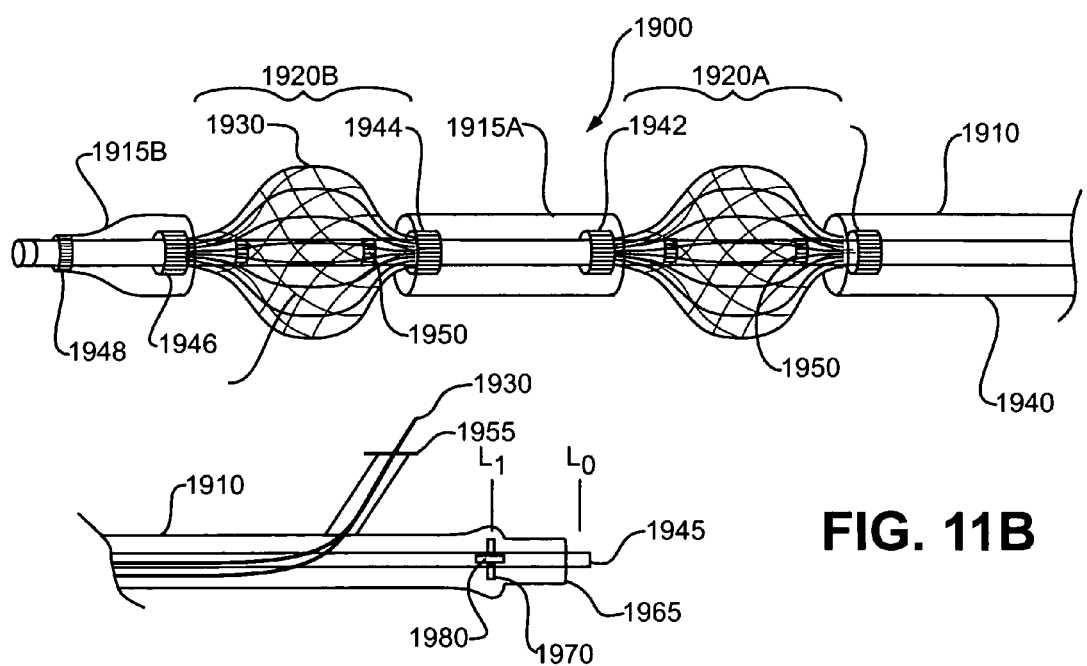
FIG. 11B shows the catheter assembly of FIG. 11A with the cage portions in a radially-expanded or open configuration.

FIGS. 11A-11B illustrate another embodiment of a coaxially-aligned catheter assembly. Catheter assembly 1900 includes inner cannula 1945 having a lumen therethrough of a diameter suitable for catheter assembly 1900 to be placed over a guidewire and positioned at a region of interest within a blood vessel of a patient. Inner cannula 1945 may be an MR compatible material such as PEEK or braided nylon. To position catheter assembly 1900, inner cannula 1945 may include a number of passive markers 1950. In one embodiment, passive markers 1950 include, but are not limited to, flat wires of titanium, tantalum, etc. bonded to inner cannula 1945 suitable for passive imaging by MR imaging systems.

In addition to inner cannula 1945, catheter assembly 1900 includes outer cannula 1910. Outer cannula 1910 has a lumen therethrough of a size suitable to accommodate inner cannula 1945. Outer cannula 1910 may be an MR compatible material such as PEEK or braided nylon. A distal portion of outer cannula 1910 includes one or more cages (cage 1920A, cage 1920B). Cage 1920A and cage 1920B, illustrated in this example, are braided segment portions, such as braided wires. Representatively, each segment portion (e.g., wire) of cage 1920A and cage 1920B may have a diameter on the order of 0.001 inches to 0.01 inches. The braided segment portions of cage 1920A and cage 1920B are braided such that cage 1920A and cage 1920B expand or collapse in response to a longitudinal force applied at a proximal end of outer cannula 1910. Disposed between cage 1920A and cage 1920B, in this embodiment, is segment portion 1915A. Segment portion 1915A may be a material similar to and have a shape similar to outer cannula 1910. Similarly, at a distal end of catheter assembly 1900 is segment 1915B (also possibly of a material similar to that of outer cannula 1910) that is connected (e.g., bonded) at a proximal end to cage 1920B and a distal end to inner cannula 1945. A distal end of segment 1915B tapers toward the profile (exterior diameter) of inner cannula 1945. In the collapsed view shown in FIG. 11A, a profile and/or diameter of catheter assembly shows outer cannula 1910, cage 1920A, cage 1920B, segment 1915A, and a portion of segment 1915B having a similar profile or diameter. Cage portion 1920A is connected to outer cannula 1910 (at a proximal end) and segment 1915A (at a distal end) through, in one embodiment, soldered rings 1940 and 1942, respectively, within a lumen of outer cannula 1910 and a lumen of segment 1915A. Similarly, a proximal end of cage 1920 is connected to segment 1915A and a distal end of cage 1920B is connected to segment 1915B by soldered rings disposed in the lumen of segment 1915A and the lumen of segment 1915B.

In one embodiment, cage 1920A and cage 1920B are formed of conductive element(s) 1930 that may be suitable as MR imaging element(s). In the case of multiple conductive elements, two or more conductive elements may be connected to one another to modify the imaging capabilities of respective conductive elements. Similarly, conductive element(s)

1930 of cage 1920A and conductive element(s) 1930 of cage 1920B may connect with one another or may be separate from one another. In another embodiment, one of cage 1920A and cage 1920B includes conductive element(s) 1930 suitable for use in imaging applications (e.g., MR imaging) while the other cage serves as an alignment device for aligning (e.g., centering) catheter assembly 1900 within a blood vessel. Conductive elements 1930 extend, in the embodiment shown in FIG. 11A through entry port 1955 at a proximal end of outer cannula 1910. Conductive element(s) 1930 may be connected to imaging circuitry, such as MR imaging circuitry, external to catheter assembly 1900.

In another embodiment, cage 1920A and cage 1920B are each used for alignment purposes and a separate imaging device is utilized with catheter assembly 1900. One suitable device is an MR antenna having dimensions suitable for positioning through inner cannula 1945 (e.g., through entry port 1965) to a region of interest (e.g., possibly as a guidewire or through a guidewire cannula).

In one embodiment, cage 1920A and cage 1920B of catheter assembly 1900 respond to a longitudinal force applied at a proximal end of outer cannula 1910. In one embodiment, a response is either to radially expand (open) or collapse (close) the cage or cages. In one embodiment, a longitudinal force applied to outer cannula 1910 in a direction toward the distal end of catheter assembly 1900 radially expands or opens cage 1920A and cage 1920B in the sense that a lateral diameter of cage 1920A is increased to a size approximating the inner diameter of a blood vessel into which catheter assembly 1900 is positioned. FIG. 11A shows catheter assembly 1900 with cage 1920A and cage 1920B in a collapsed or closed orientation suitable for being advanced to a region of interest. A proximal end of the catheter assembly includes lever 1970, for example, a protuberance or protuberances on inner cannula 1945. The catheter assembly also includes lock 1980 at position, $L_0$, that may be, for example, an opening in outer cannula 1910. Outer cannula 1910 may be forced by a pushing action in a longitudinal (distal) direction to a distance where it may be set through lock 1980. In another embodiment, cage 1920A and cage 1920B may be disposed over balloon portions of a balloon catheter with the balloon portions being separately or collectively inflatable to expand cage 1920A and cage 1920B.

FIG. 11B shows catheter assembly 1900 with cage 1920A and cage 1920B in a racially-expanded or open configuration. FIG. 11B illustrates the longitudinal force applied to outer cannula 1910 through the movement of lever 1970 to position, $L_1$, aligned with lock 1980. The locking of lever 1970 allows catheter assembly 1900 to be retained at a region of interest with cage 1920A and cage 1920B in a radially-expanded or open position. Through the use of one or more braided cages such as 1920A and 1920B, fluid (e.g., blood) perfusion may be achieved while catheter assembly 1900 is at a region of interest within a blood vessel of a patient. In other words, the braided cage, in one embodiment, has sufficient openings therethrough to allow fluid (e.g., blood) through the cage.

Figure 12A:
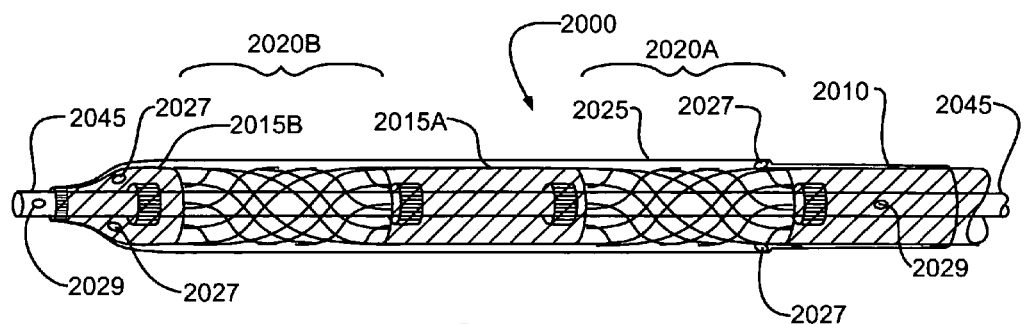
FIG. 12A illustrates a distal portion of a catheter assembly including a coaxial shaft of two cannulas with a distal portion of one cannula including a number of braided cage portions.
Figure 12B:
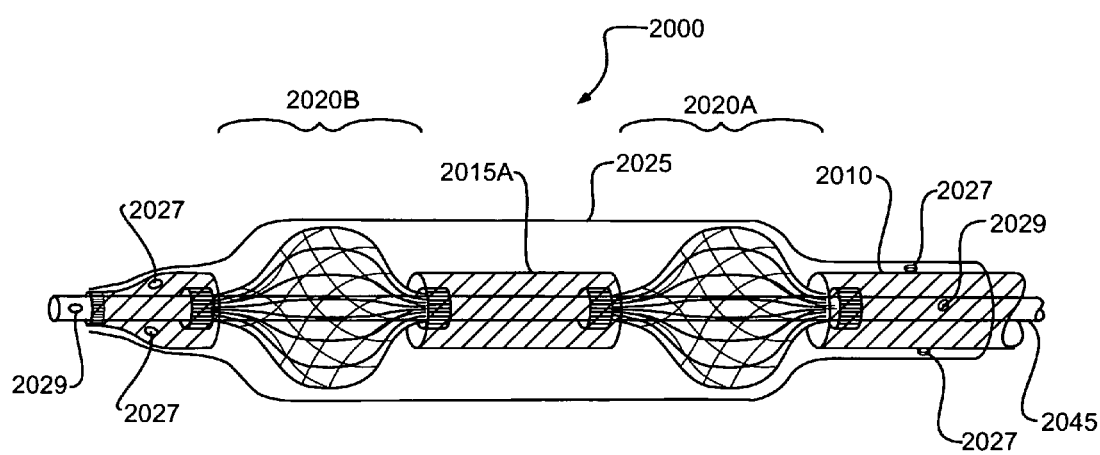
FIG. 12B shows the catheter assembly of FIG. 12A with the cage portions in a radially-expanded or open configuration.

FIG. 12A and FIG. 12B illustrate another embodiment of a coaxially-aligned catheter assembly having one or more braided cage portions. Catheter assembly 2000 is similar in many regards to catheter assembly 1900. Reference may be made to FIGS. 11A-11B and the accompanying text for many details. Referring to FIG. 12A, catheter assembly 2000 includes inner cannula 2044 disposed within a lumen of outer cannula 2010. Catheter assembly 2000 also includes cage 2020A connected between outer cannula 2010 and segment 2015A, and cage 2020B connected between segment 2015A and 2015B. In this embodiment, cage 2020A and cage 2020B are covered by sheath 2025. Sheath 2025 may be a material that is suitable for a balloon catheter and is MR compatible. Representatively, a material for sheath 2025, in one embodiment, has sufficient elasticity to expand in response to expansion of cage 2020A or cage 2020B. One suitable material is PEBAX. In one embodiment, sheath 2025 is connected at a proximal end to a distal end of outer cannula 2010 and at a distal end to segment 2015B. One way to connect polymer materials is by thermal bonding.

Catheter assembly 2000 may be used as an imaging device such as an MR imaging device. Cage 2020A and/or cage 2020B may contain conductive element(s) suitable for transmitting or receiving RF signals. Alternatively, cage 2020A and/or cage 2020B may used as alignment devices to align catheter assembly 2000 in a blood vessel of a patient. Representatively, cage 2020A and/or cage 2020B may be formed of braided segment portions (e.g., braided wires), each segment portion having a diameter on the order of 0.001 inches to 0.01 inches. In one embodiment, an imaging device such as an MR imaging antenna or coil may be positioned at a region of interest within a blood vessel through the lumen of inner cannula 2045.

To permit fluid (e.g., blood) perfusion while catheter assembly 2000 is used as an imaging device within a blood vessel of a patient, sheath 2025 may include a number of perfusion holes 2027, representatively illustrated in FIG. 11A at a proximal end and a distal end of sheath 2025. Similarly, inner cannula 2045 may also have perfusion holes 2029. FIG. 12B shows catheter assembly 2000 with cages 2020A and 2020B in A radially-expanded state. FIG. 12B also shows sheath 2025 disposed over the expanded cages. Representatively, the techniques for expanding cages 2020A and/or 2020B described above with respect to FIGS. 11A-11B may be used here. Alternatively, cage 2020A and cage 2020B may be disposed over balloon portions of a balloon catheter with the balloon portions being separately or collectively inflatable to expand cage 2020A and cage 2020B.

What is claimed is:

1. An apparatus comprising:
   a device having dimensions suitable for percutaneous delivery to a patient;
   an antenna capable of receiving magnetic resonance (MR) signals,
   wherein the antenna is associated with the device in a manner that provides at least one of a prescribed radial orientation and longitudinal orientation of the antenna at a point of interest within a blood vessel of the patient; and
   at least one conductive lead coupled with the antenna and extending proximally from the antenna, the at least one conductive lead to convey the received magnetic resonance (MR) signals from the antenna in a proximal direction,
   wherein the device comprises a primary cannula comprising a segment comprising a plurality of fillets, wherein under a first condition, the segment has a first radial dimension and under a second condition, a larger second radial dimension, and
   wherein the plurality of fillets each comprises an individual cannula portion that is a tube and are all arranged in a fillet formation coupled at a proximal end to the primary cannula, and wherein a plurality of conductive elements of the antenna are disposed in respective ones of the plurality of cannula portions.

2. The apparatus of claim 1 wherein at least one of the device and the antenna comprises a portion comprising a material that is not susceptible to magnetic resonance frequency detection.

3. The apparatus of claim 2, wherein the portion of the at least one of the device and the antenna comprises a material that is not conductive to radio frequency (RF) signals.

4. The apparatus of claim 2, wherein the antenna comprises a dipole antenna.

5. The apparatus of claim 1, wherein a portion of the antenna comprises a plurality of longitudinally disposed conductive elements circumferentially spaced at the point of interest.

6. The apparatus of claim 5, wherein a portion of the plurality of conductive elements are coupled at one end.

7. The apparatus of claim 6, wherein the portion of the plurality of conductive elements are coupled at the one end and collectively define an ellipse.

8. The apparatus of claim 6, wherein the plurality of conductive elements each comprise a first material and a second material on the first material that has a conductivity greater than the first material.

9. The apparatus of claim 5, wherein a first portion of the plurality of conductive elements yields a first periodic function in response to a radio frequency signal and a second portion of the conductive elements yields a second different periodic function.

10. The apparatus of claim 5, wherein a portion of the plurality of conductive elements are coupled together and yield, in the presence of a radio frequency signal, a reception that is greater than a reception of one or more of the plurality of conductive elements that are not coupled together.

11. The apparatus of claim 5, wherein the plurality of conductive elements are selected from tubing, wires, ribbons, and deposited conductive materials.

12. The apparatus of claim 11, wherein a portion of each of the plurality of conductive elements is electrically insulated.

13. The apparatus of claim 1, wherein the device comprises a plurality of markers susceptible to detection under magnetic radio frequency imaging about its length.

14. The apparatus of claim 1, further comprising radio frequency receiving circuitry proximal to the antenna, wherein the antenna is coupled to the radio frequency receiving circuitry.

15. The apparatus of claim 1, wherein at a largest point, the second radial dimension approximates an inner diameter of the blood vessel at the point of interest.

16. The apparatus of claim 1, further comprising a secondary cannula disposed within the primary cannula and distally extending through the segment of the plurality of fillets.

17. The apparatus of claim 1, wherein the device comprises a primary cannula comprising a plurality of segments along a length of the cannula, each segment comprising a plurality of fillets wherein under a first condition, each segment has a first radial dimension and under a second condition, a larger second radial dimension.

18. The apparatus of claim 17, wherein the antenna is wrapped around one of an exterior of the primary cannula between at least two of the plurality of segments and within at least one segment.

19. The apparatus of claim 18, wherein the antenna is wrapped at a first location in a first direction and at a second location in a different second direction.

20. The apparatus of claim 1, wherein the antenna comprises a plurality of conductive elements coupled in a phase relationship with respect to one another.

21. The apparatus of claim 1, further comprising imaging circuitry coupled with the at least one conductive lead to generate images based on the signals.

22. The apparatus of claim 1, further comprising a magnetic resonance (MR) processing system coupled with the at least one conductive lead to process the signals.

23. The apparatus of claim 1, further comprising a circuit at a proximal portion of the device to receive the signals from the at least one conductive lead.

24. The apparatus of claim 1, further comprising a tuning capacitor coupled with the antenna.

25. An apparatus comprising:
a device having dimensions suitable for percutaneous delivery to a patient, wherein the device comprises a cannula comprising a plurality of cannula segments that are each a tube and are all arranged in a fillet formation joining at a distal end into a single cannula segment wherein under a first condition, the plurality of cannula segments have a collective first radial dimension and under a second condition, a larger second radial dimension;
an antenna capable of receiving magnetic resonance (MR) signals, wherein the antenna comprises a plurality of antenna segments disposed within respective ones of the plurality of cannula segments,
wherein the antenna is associated with the device in a manner that provides at least one of a prescribed radial orientation and longitudinal orientation of the antenna at a point of interest within a blood vessel of the patient; and
at least one conductive lead coupled with the antenna and extending proximally from the antenna, the at least one conductive lead to convey the received magnetic resonance (MR) signals from the antenna in a proximal direction.

26. The apparatus of claim 25, wherein at a largest point, the second radial dimension approximates an inner diameter of the blood vessel at the point of interest.

27. The apparatus of claim 25, wherein the cannula is a primary cannula and the device further comprises a secondary cannula disposed within the primary cannula through the single cannula segment and the antenna is disposed in the secondary cannula.

28. A method comprising:
inserting a medical device comprising an antenna capable of receiving radio frequency signals in a blood vessel of a patient;
at least one of radially orienting and longitudinally orienting the antenna at a point of interest within a blood vessel of the patient; and
conveying radio frequency signals received by the antenna to imaging circuitry,
wherein the device comprises a primary cannula comprising a segment comprising a plurality of fillets, wherein under a first condition, the segment has a first radial dimension and under a second condition, a larger second radial dimension,
wherein the plurality of fillets each comprises an individual cannula portion that is a tube and are all arranged in a fillet formation coupled at a proximal end to the primary cannula, and wherein a plurality of conductive elements of the antenna are disposed in respective ones of the plurality of cannula portions, and
wherein the antenna comprises a plurality of longitudinally disposed conductive elements associated with respective ones of the plurality of fillets and wherein orienting the antenna comprises positioning the conductive elements adjacent to a wall of the blood vessel at the point of interest.

29. The method of claim 28, wherein inserting the medical device comprises percutaneously inserting the medical device.

30. The method of claim 28, wherein orienting the antenna comprises positioning a portion of the medical device adjacent to a wall of the blood vessel at the point of interest.

31. The method of claim 30, wherein at the point of interest the antenna is positioned between the portion of the medical device and the wall of the blood vessel.

32. The method of claim 30, wherein at the point of interest the portion of the medical device is disposed between the antenna and the wall of the blood vessel.

33. The method of claim 28, further comprising imaging the point of interest from signals received from the antenna.

34. The method of claim 28, further comprising positioning the antenna-by imaging the blood vessel while advancing the medical device.

35. The method of claim 28, wherein conveying comprises conveying the radio frequency signals over at least one signal line coupled with the antenna and extending from the antenna in a proximal direction.

36. The method of claim 28, further comprising generating an image of the point of interest based on the radio frequency signals conveyed to the imaging circuitry.

37. The method of claim 28, further comprising receiving the radio frequency signals with the antenna, including receiving radio frequency signals that have a phase relationship in which they are separated in phase from one another.

* * * * *